United States Patent
Kawaguchi et al.

[11] Patent Number: 5,820,746
[45] Date of Patent: Oct. 13, 1998

[54] METAL SURFACE STATE EVALUATION METHOD AND SEMICONDUCTOR DEVICE PRODUCTION METHOD

[75] Inventors: Akemi Kawaguchi, Osaka; Nobuo Aoi, Hyogo, both of Japan

[73] Assignee: Matsushita Electric Industrial Co., Ltd., Osaka, Japan

[21] Appl. No.: 689,763

[22] Filed: Aug. 13, 1996

[30] Foreign Application Priority Data

Aug. 24, 1995 [JP] Japan ................................ 7-215829
Jun. 6, 1996 [JP] Japan ................................ 8-143987
Aug. 12, 1996 [JP] Japan ................................ 8-054577

[51] Int. Cl.$^6$ ............................ G01N 27/26; H01L 21/66
[52] U.S. Cl. ......................... 205/791; 204/404; 204/434; 205/775.5; 205/790.5; 205/791.5; 438/14; 438/17; 438/584
[58] Field of Search ..................... 204/404, 434; 205/775.5, 776, 790.5, 791, 791.5; 156/626.1, 627.1; 216/59.61, 84.86; 438/14.17, 584

[56] References Cited

U.S. PATENT DOCUMENTS

| | | | |
|---|---|---|---|
| 3,479,256 | 11/1969 | Smith et al. | 204/404 |
| 4,338,157 | 7/1982 | Kanda | 156/627 |
| 4,425,193 | 1/1984 | Taylor | 205/775.5 |
| 4,511,844 | 4/1985 | Tietze | 324/425 |
| 4,629,536 | 12/1986 | Kadin et al. | 204/434 |
| 5,188,715 | 2/1993 | Chen et al. | 204/153 |
| 5,448,178 | 9/1995 | Chen et al. | 324/700 |

FOREIGN PATENT DOCUMENTS

| | | |
|---|---|---|
| 0 591 802 | 4/1994 | European Pat. Off. |
| 62-250350 | 10/1987 | Japan |
| 63-317759 | 12/1988 | Japan |
| 62-201635 | 7/1994 | Japan |

*Primary Examiner*—T. Tung
*Attorney, Agent, or Firm*—McDermott, Will & Emery

[57] ABSTRACT

Metal formed on a semiconductor wafer is brought into contact with ions adapted to corrode the metal, and subjected to constant-current electrolysis using a galvanostat. The electrode potential of the metal is measured. There are obtained (i) the relationship between current value and time of pitting corrosion and (ii) the critical current value, based on which the metal is evaluated for surface smoothness, the pitting corrosion resistance of metal surface, resistance to pitting corrosion, the segregation amount and concentration of trace metal contained in the metal, and the grain size or grain boundary length of the metal.

13 Claims, 18 Drawing Sheets

METAL SURFACE STATE EVALUATION METHOD AND SEMICONDUCTOR DEVICE PRODUCTION METHOD

BACKGROUND OF THE INVENTION

The present invention relates to a method of evaluating, in an in-line, nondestructive and quantitative manner in a short period of time, the surface state and corrosive properties of metal to be used, for example, for wiring on a semiconductor substrate, and also relates to a semiconductor device production method using the first-mentioned method.

The surface state of metal exerts a great influence upon corrosion thereof. For example, an aluminum layer used for wiring on a semiconductor substrate is improved in corrosion resistance by a natural oxide layer finely formed on the surface thereof.

In an aluminum layer, a difference in potential is formed between aluminum and copper added in several percents to the aluminum for improving the resistance to electromigration of the aluminum layer. Accordingly, as the segregation amount of copper on the surface of the aluminum layer is greater, many local cells are formed, causing the aluminum layer to be readily corroded.

Accordingly, knowledge of the surface state of a metal permits evaluation of the corrosion resistance thereof.

As the metal surface state evaluation method, there is proposed a physical analysis of which examples include a direct observation method using TEM (Transmission Electron Microscope), a layer thickness measurement method using AES (Auger Electron Spectroscopy), a bond-state evaluation method using XPS (X-ray Photo-emission Spectroscopy), a segregation amount measurement method using a plane SIMS (Secondary Ion Mass Spectrometer) and the like.

According to each of the conventional metal surface state evaluation methods above-mentioned, however, metal to be evaluated is cut to form a sample and an electron beam, X-rays or ions are then incident upon the sample for measurement. Accordingly, each of the methods above-mentioned is a destructive analysis method and takes time for sample preparation and measurement, and is therefore disadvantageous in that it is difficult to use such a method as an in-line analysis method (analysis incorporated in a semiconductor device mass-production line). Further, each of the conventional metal surface state evaluation methods above-mentioned is disadvantageous in that no quantitative evaluation can be made on corrosive properties.

SUMMARY OF THE INVENTION

To overcome the conventional problems above-mentioned, the present invention is proposed with the object of evaluating, in an in-line manner in a short period of time, the surface state of a metal for corrosion resistance, surface smoothness, the pitting corrosion resistance of a surface layer, the segregation amount or concentration of trace metal contained in the metal, the grain size or grain boundary length of the metal and the like, such evaluation being quantitatively made without a specimen of the metal being broken.

To achieve the object above-mentioned, a first metal surface state evaluation method according to the present invention, comprises: a solution contacting step of bringing metal into contact with a solution containing ions to corrode the metal; a metal corroding step of applying, to the solution, each of a plurality of constant electric currents respectively having different current values, causing the metal to be corroded by the solution; an electrode potential measuring step of measuring, at each of the electric currents, the electrode potential of the metal which is being corroded by the solution; a change ratio calculating step of calculating, based on the electrode potential at each of the electric currents, a ratio of changes in time of pitting corrosion to changes in current value; and a dissolving speed measuring step of measuring, based on the change ratio, a speed at which an oxide layer formed on the metal surface is dissolved.

According to the first metal surface state evaluation method, metal is subjected, as contacted with a solution containing ions to corrode the metal, to constant-current electrolysis, and the electrode potential of the metal is measured. Based on the electrode potential thus measured, there is calculated a ratio of changes in time of pitting corrosion to changes in current value. Using the fact that the slope of a graphic line illustrating the relationship between the ratio of changes in time of pitting corrosion and the concentration of the solution, shows a dissolving speed of an oxide layer formed on the metal surface, the dissolving speed of the oxide layer can be measured based on the ratio of changes in time of pitting corrosion. Accordingly, based on the relationship between the ratio of changes in time of pitting corrosion of the metal to changes in current value and the dissolving speed of the oxide layer formed on the metal surface, the oxide layer dissolving speed can be measured in an in-line manner in a short period of time without breaking the metal.

Preferably, the first metal surface state evaluation method further comprises a smoothness evaluating step of evaluating the surface smoothness of the metal based on the oxide layer dissolving speed. According to the arrangement above-mentioned, based on the relationship between oxide layer dissolving speed and metal surface smoothness, the metal surface smoothness can quantitatively be evaluated in an in-line manner in a short period of time without breaking the metal.

Preferably, the first metal surface state evaluation method further comprises a pitting corrosion resistance evaluating step of evaluating the pitting corrosion resistance of the oxide layer based on the oxide layer dissolving speed. According to the arrangement above-mentioned, based on the relationship between oxide layer dissolving speed and pitting corrosion resistance of oxide layer, the pitting corrosion resistance of the oxide layer can quantitatively be evaluated in an in-line manner in a short period of time without breaking the metal.

A second metal surface state evaluation method according to the present invention comprises: a solution contacting step of bringing metal into contact with a solution containing ions to corrode the metal; a metal corroding step of applying, to the solution, each of a plurality of constant electric currents respectively having different current values, causing the metal to be corroded by the solution; an electrode potential measuring step of measuring, at each of the electric currents, the electrode potential of the metal which is being corroded by the solution; a pitting-corrosion time calculating step of calculating, based on the electrode potential at each of the current values, a relationship between current value and time of pitting corrosion; a critical current value calculating step of calculating, based on the relationship between current value and time of pitting corrosion, a critical current value which is the minimum current value at which pitting corrosion starts occurring; and a pitting-corrosion property evaluating step of evaluating, based on the critical current value, the pitting corrosion property of the metal.

According to the second metal surface state evaluation method, metal is subjected, as contacted with a solution containing ions adapted to corrode the metal, to constant current electrolysis, and the electrode potential of the metal is measured. Based on the electrode potential thus measured, there is calculated the relationship between current value and time of pitting corrosion. Based on the relationship between current value and time of pitting corrosion, the critical current value of the metal is calculated. Using the fact that pitting corrosion more readily occurs as the critical current value is smaller, the pitting corrosion property of the metal can quantitatively be evaluated based on the critical current value. Accordingly, based on the relationship between critical current value and pitting corrosion property of the metal, the pitting corrosion property of the metal can quantitatively be evaluated in an in-line manner in a short period of time without breaking the metal.

Preferably, the second metal surface state evaluation method further comprises a grain size or grain boundary length evaluating step of evaluating the grain size or grain boundary length of the metal based on the critical current value. According to the arrangement above-mentioned, based on the relationship between the critical current value of the metal and the grain size or grain boundary length of the metal, the grain size or grain boundary length of the metal can quantitatively be evaluated in an in-line manner in a short period of time without breaking the metal.

A third metal surface state evaluation method according to the present invention comprises: a solution contacting step of bringing an alloy containing a trace amount of metal, into contact with a solution containing ions to corrode the alloy; an alloy corroding step of applying, to the solution, each of a plurality of constant electric currents respectively having different current values, causing the alloy to be corroded by the solution; an electrode potential measuring step of measuring, at each of the electric currents, the electrode potential of the alloy which is being corroded by the solution; a pitting-corrosion time calculating step of calculating, based on the electrode potential at each of the current values, a relationship between current value and time of pitting corrosion; a critical current value calculating step of calculating, based on the relationship between current value and time of pitting corrosion, a critical current value which is the minimum current value at which pitting corrosion starts occurring; and a segregation amount or concentration evaluating step of evaluating, based on the critical current value, the segregation amount or concentration of the metal in the alloy.

According to the third metal surface state evaluation method, an alloy containing trace metal is subjected, as contacted with a solution containing ions to corrode the alloy, to constant-current electrolysis, and the electrode potential of the alloy is measured. Based on the electrode potential thus measured, there is calculated the relationship between current value and time of pitting corrosion, based on which the critical current value of the alloy is calculated. Using the fact that when the amount of the trace metal segregated in the boundary of the alloy crystal grains is increased, pitting corrosion more readily occurs and the critical current value is therefore reduced, the segregation amount or concentration of the metal in the alloy can quantitatively be evaluated based on the critical current value. Accordingly, based on the relationship between the critical current value of the alloy and the segregation amount or concentration of the metal in the alloy, the segregation amount or concentration of the metal in the alloy can quantitatively be evaluated in an in-line manner in a short period of time without cutting the alloy.

A fourth metal surface state evaluation method according to the present invention comprises: a solution contacting step of bringing a metallic thin layer into contact with a solution containing ions to corrode the metallic thin layer; a metallic thin layer corroding step of applying, to the solution, each of a plurality of constant electric currents respectively having different current values, causing the metallic thin layer to be corroded by the solution; an electrode potential measuring step of measuring, at each of the electric currents, the electrode potential of the metallic thin layer which is being corroded by the solution; a pitting-corrosion time calculating step of calculating, based on the electrode potential at each of the current values, a relationship between current value and time of pitting corrosion; a change ratio calculating step of calculating, based on the electrode potential at each of the electric currents, a ratio of changes in time of pitting corrosion to changes in current value; a critical current value calculating step of calculating, based on the relationship between current value and time of pitting corrosion, a critical current value which is the minimum current value at which pitting corrosion starts occurring; and a corrosion resistance evaluating step of evaluating the corrosion resistance of the metallic thin layer based on the change ratio and the critical current value.

According to the fourth metal surface state evaluation method, a metallic thin layer is subjected, as contacted with a solution containing ions adapted to corrode the metallic thin layer, to constant-current electrolysis, and the electrode potential of the metallic thin layer is measured. Based on the electrode potential thus measured, there are calculated the relationship between current value and time of pitting corrosion and a ratio of changes in time of pitting corrosion to changes in current value. Based on the relationship between current value and time of pitting corrosion, the critical current value of the metallic thin layer is calculated. Thus, there can be evaluated (i) the surface smoothness of the metallic thin layer and the pitting corrosion resistance of the oxide layer formed on the surface of the metallic thin layer, each of which relates to the ratio of changes in time of pitting corrosion, and (ii) the resistance to pitting corrosion of the metallic thin layer, the segregation amount or concentration of contained trace metal, and the grain size or grain boundary length of Al, each of which relates to the critical current value. Accordingly, based on the change ratio and the critical current value, the corrosion resistance of the metallic thin layer can quantitatively be evaluated in an inline manner in a short period of time without breaking the metallic thin layer.

A fifth metal surface state evaluation method according to the present invention comprises: a solution contacting step of bringing metal into contact with a solution containing ions to corrode the metal; a metal corroding step of applying a constant potential to the solution, causing the metal to be corroded by the solution; a corrosion current measuring step of measuring changes, with the passage of time, in corrosion current of the metal which is being corroded by the solution; a no-pitting-corrosion time measuring step of measuring, based on the changes in corrosion current with the passage of time, a period of time during which no pitting corrosion is occurring; and a pitting corrosion resistance evaluating step of evaluating, based on the no-pitting-corrosion time, the pitting corrosion resistance of an oxide layer formed on the surface of the metal.

According to the fifth metal surface state evaluation method, metal is subjected, as contacted with a solution containing ions adapted to corrode the metal, to constant potential electrolysis, and the corrosion current of the metal is measured. Based on the corrosion current thus measured, the time of no pitting corrosion is measured. Using the fact that the pitting corrosion resistance of the oxide layer formed on the metal surface is greater as the time of no pitting corrosion is longer, the pitting corrosion resistance of the oxide layer can quantitatively be evaluated based on the time of no pitting corrosion. Accordingly, based on the relationship between time of no pitting corrosion of the metal and the pitting corrosion resistance of the oxide layer formed on the metal surface, the pitting corrosion resistance of the oxide layer can quantitatively be evaluated in an in-line manner in a short period of time without cutting the metal.

A sixth metal surface state evaluation method according to the present invention comprises: a solution contacting step of bringing metal into contact with a solution containing ions to corrode the metal; a metal corroding step of applying a constant potential to the solution, causing the metal to be corroded by the solution; a maximum corrosion current measuring step of measuring the maximum corrosion current having the highest value out of corrosion currents of the metal which is being corroded by the solution; and a corrosion resistance evaluating step of evaluating the corrosion resistance of the metal based on the maximum corrosion current.

According to the sixth metal surface state evaluation method, metal is subjected, as contacted with a solution containing ions to corrode the metal, to constant-potential electrolysis, and the maximum corrosion current of the metal is measured. Using the fact that the corrosion resistance of the metal is greater as the maximum current density proportional to the maximum corrosion current of the metal is smaller, the corrosion resistance of the metal can quantitatively be evaluated. Accordingly, based on the relationship between the maximum corrosion current of the metal and the corrosion resistance of the metal, the corrosion resistance of the metal can quantitatively be evaluated in an in-line manner in a short period of time without cutting the metal.

In each of the fifth and sixth metal surface state evaluation methods, the constant potential to be applied at the metal corroding step, preferably has a value in the vicinity of the natural electrode potential of the metal. According to the arrangement above-mentioned, when measuring the corrosion current while subjecting, to constant-potential electrolysis, metal as contacted with a solution containing ions adapted to corrode the metal, no electric field is applied to the metal since the constant potential to be applied has a value in the vicinity of the natural electrode potential. Thus, in the state where the metal naturally corrodes in the solution, the corrosion current value can be measured.

A first semiconductor device production method according to the present invention comprises: a metallic thin layer forming step of forming a metallic thin layer on a semiconductor substrate under predetermined deposit conditions; a solution contacting step of bringing the metallic thin layer into contact with a solution containing ions to corrode the metallic thin layer; a metallic thin layer corroding step of applying, to the solution, each of a plurality of constant electric currents respectively having different current values, causing the metallic thin layer to be corroded by the solution; an electrode potential measuring step of measuring, at each of the electric currents, the electrode potential of the metallic thin layer which is being corroded by the solution; a pitting corrosion time calculating step of calculating, based on the electrode potential at each of the current values, a relationship between current value and time of pitting corrosion; a change ratio calculating step of calculating, based on the electrode potential at each of the electric currents, a ratio of changes in time of pitting corrosion to changes in current value; a critical current value calculating step of calculating, based on the relationship between current value and time of pitting corrosion, a critical current value which is the minimum current value at which pitting corrosion starts occurring; and a deposit condition judging step of evaluating the surface state of the metallic thin layer based on the change ratio and the critical current value, and judging, based on the evaluation thus made, whether or not the predetermined deposit conditions at the metallic thin layer forming step are suitable.

According to the first semiconductor device production method, a metallic thin layer formed on a semiconductor substrate under predetermined deposit conditions, is subjected, as contacted with a solution containing ions to corrode the metallic thin layer, to constant-current electrolysis, and the electrode potential of the metallic thin layer is measured. Based on the electrode potential thus measured, there are calculated the relationship between current value and time of pitting corrosion and a ratio of changes in time of pitting corrosion to changes in current value. Based on the relationship between current value and time of pitting corrosion, the critical current value of the metallic thin layer is calculated. Thus, there can be evaluated (i) the surface smoothness of the metallic thin layer and the pitting corrosion resistance of an oxide layer formed on the surface of the metallic thin layer, each of which relates to the ratio of changes in time of pitting corrosion, and (ii) the resistance to pitting corrosion of the metallic thin layer, the segregation amount or concentration of contained trace metal, and the grain size or grain boundary length of Al, each of which relates to the critical current value. Accordingly, the metallic thin layer can be evaluated for surface state, and based on the evaluation thus made, a judgement can be made of whether or not the predetermined deposit conditions at the metallic thin layer forming process are suitable. Accordingly, the surface state of the metallic thin layer formed on a semiconductor substrate under predetermined deposit conditions can be evaluated based on the ratio of changes in time of pitting corrosion to changes in current value and on the critical current value. Based on the evaluation thus made, a judgement can be made of whether or not the predetermined deposit conditions used in the metallic thin layer forming process are suitable. Thus, the metallic thin layer deposit conditions can be determined in a short period of time.

A second semiconductor device production method according to the present invention comprises: a step of forming metallic wiring on a semiconductor substrate; a step of forming an oxide layer on the metallic wiring; a solution contacting step of bringing the metallic wiring having the oxide layer formed thereon, into contact with a solution containing ions to corrode the metallic wiring; a metallic wiring corroding step of pitting corrosion to changes in current value. Accordingly, there can be evaluated the pitting corrosion resistance of the oxide layer which relates to the ratio of changes in time of pitting corrosion. Thus, the oxide layer can be evaluated for corrosion resistance. Accordingly, in a metallic wiring having an oxide layer formed on the surface thereof, the corrosion resistance of the oxide layer can be evaluated based on the relationship between (i) the ratio of changes in time of pitting corrosion to changes in current value and (ii) the pitting corrosion resistance of the oxide layer. Based on the evaluation thus made, the corrosion resistance of the oxide layer is compared with a predetermined standard. Based on the result of such comparison, a judgement can be made of whether or not the oxide layer is good. Such a judgment can be made in an in-line manner in a short period of time without cutting the metallic wiring. Further, an oxide layer which does not satisfy the predetermined standard, can be modified. This greatly contributes to improvements in production yield of semiconductor devices.

According to the second semiconductor device production method, metallic wiring having an oxide layer formed on the surface thereof is subjected, as contacted with a solution containing ions to corrode the metallic wiring, to constant current electrolysis, and the electrode potential of the metallic wiring is measured. Based on the electrode potential thus measured, there is calculated a ratio of changes in time.

Figure 3A:
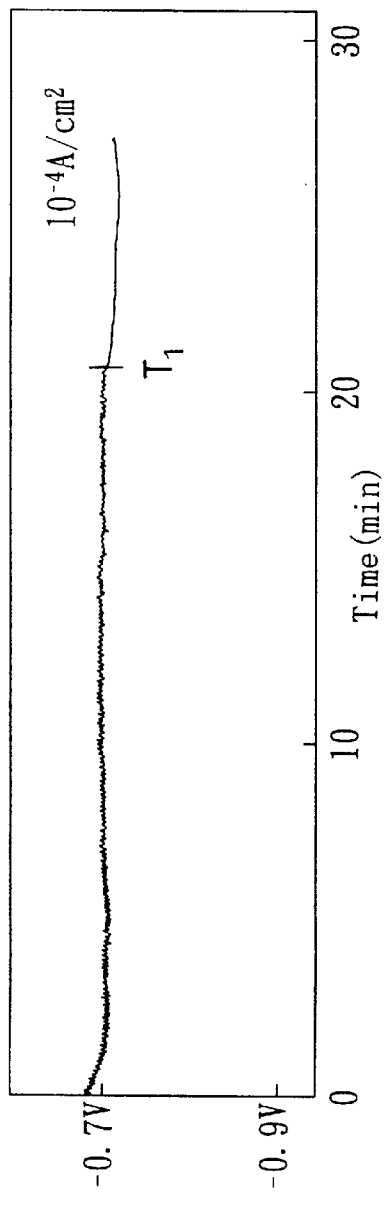
Figure 4A:
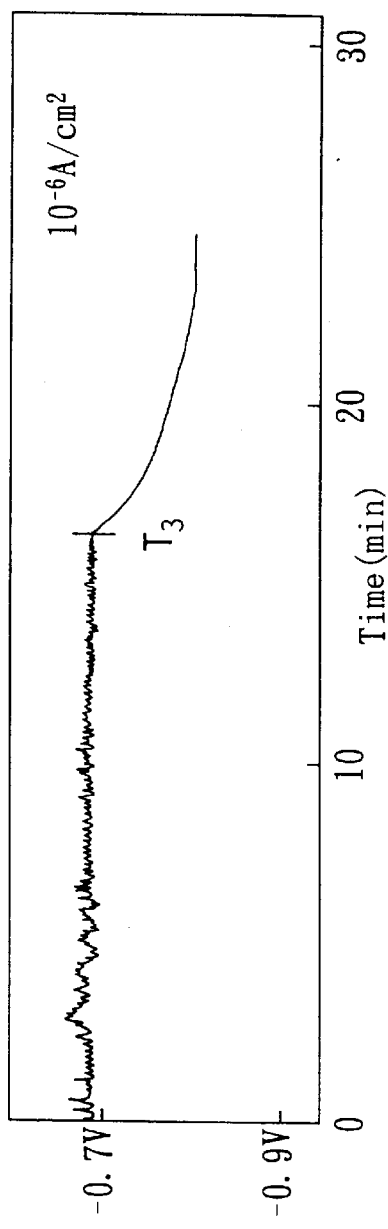
Figure 5:
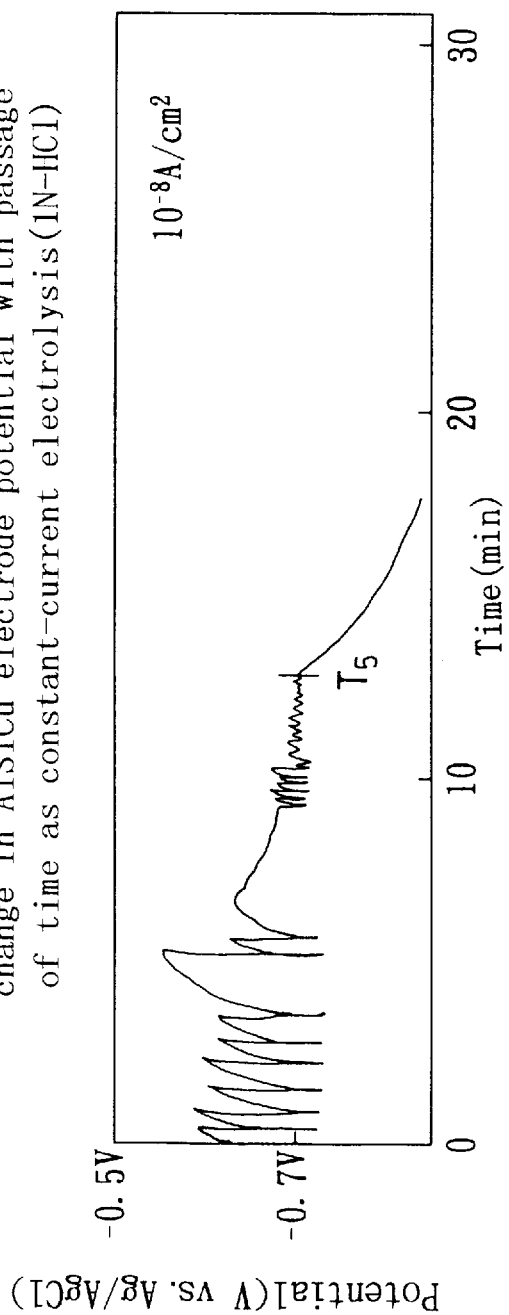
Figure 6:
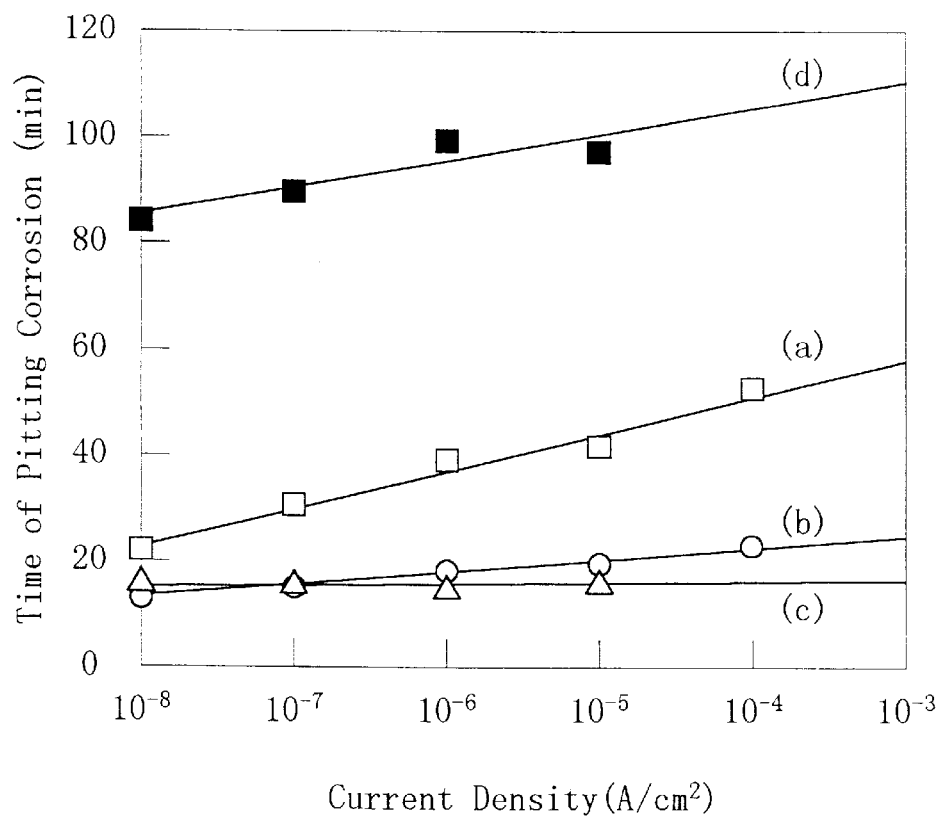
Figure 7A:
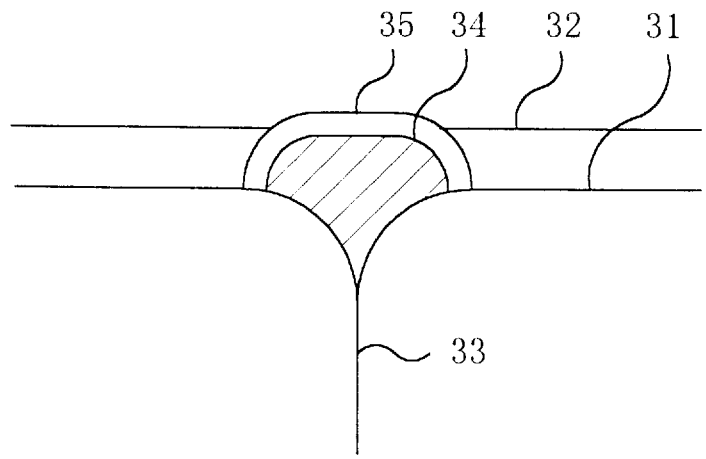
Figure 8:
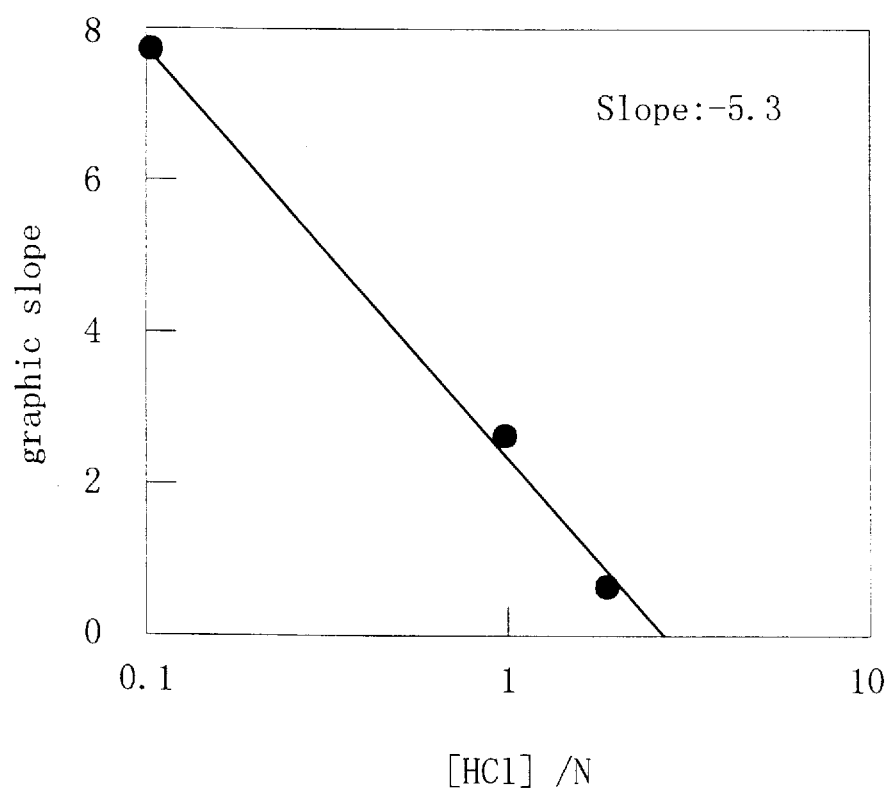
Figure 9:
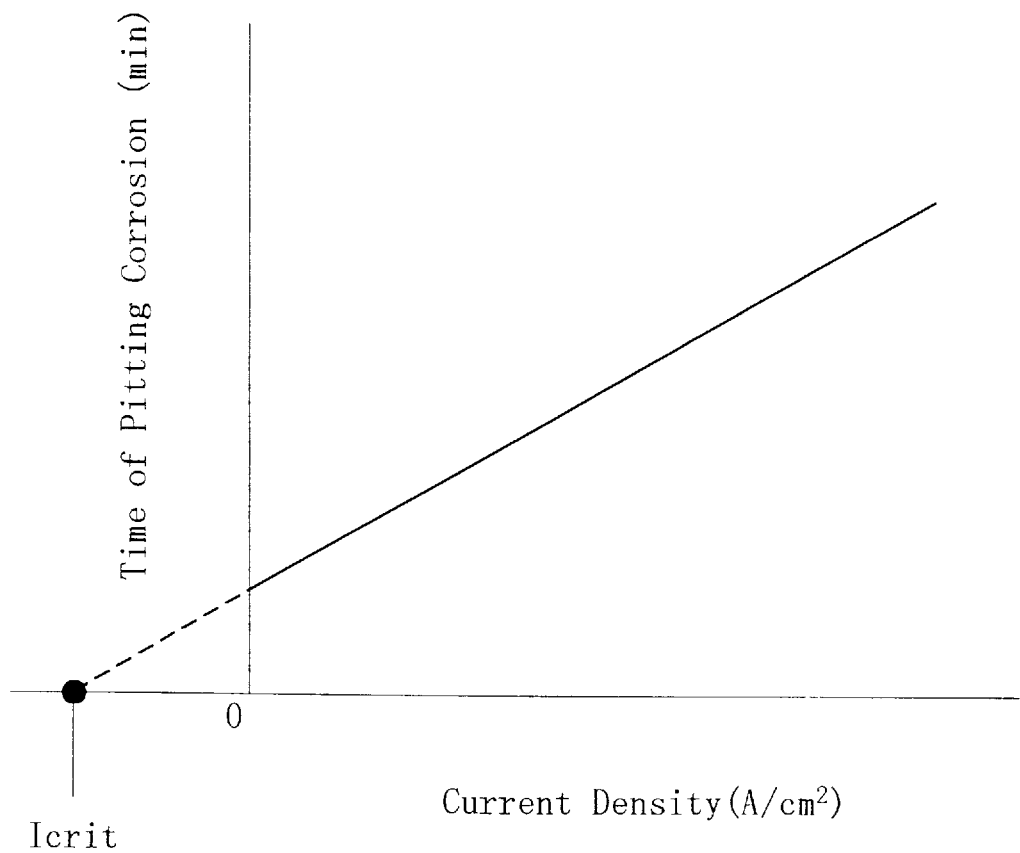
Figure 10:
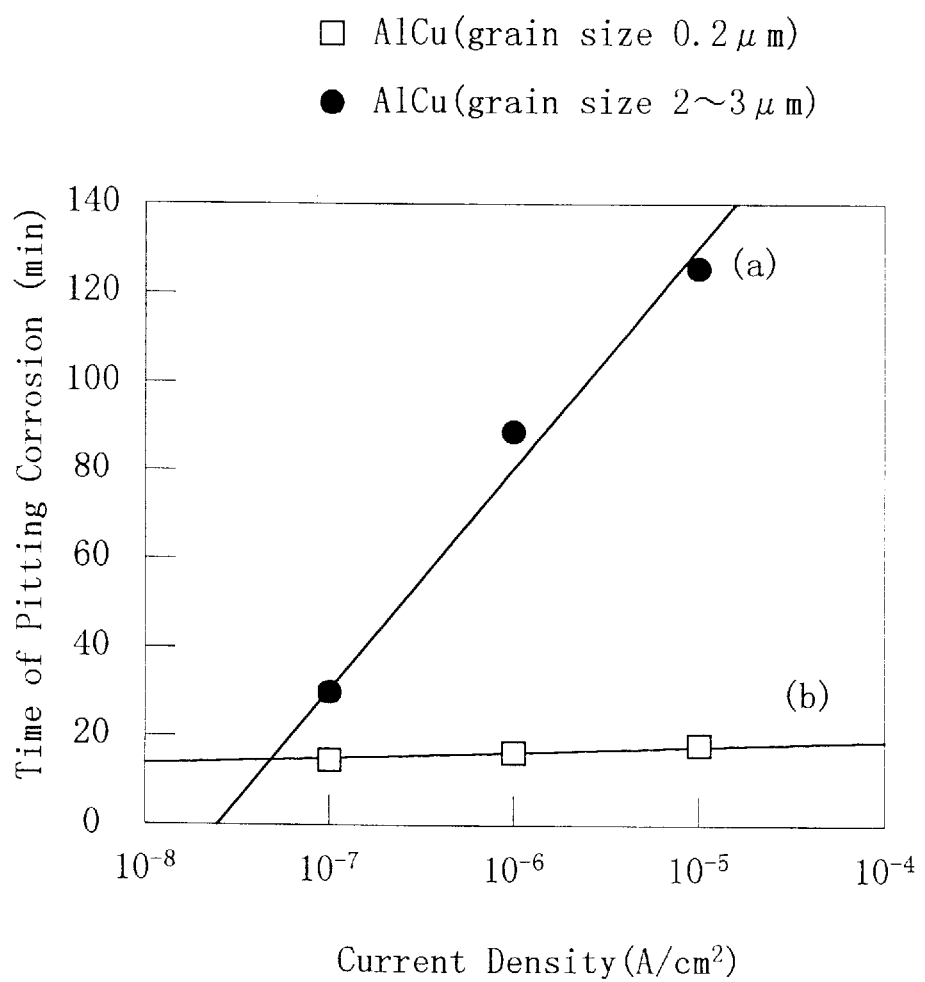
Figure 11:
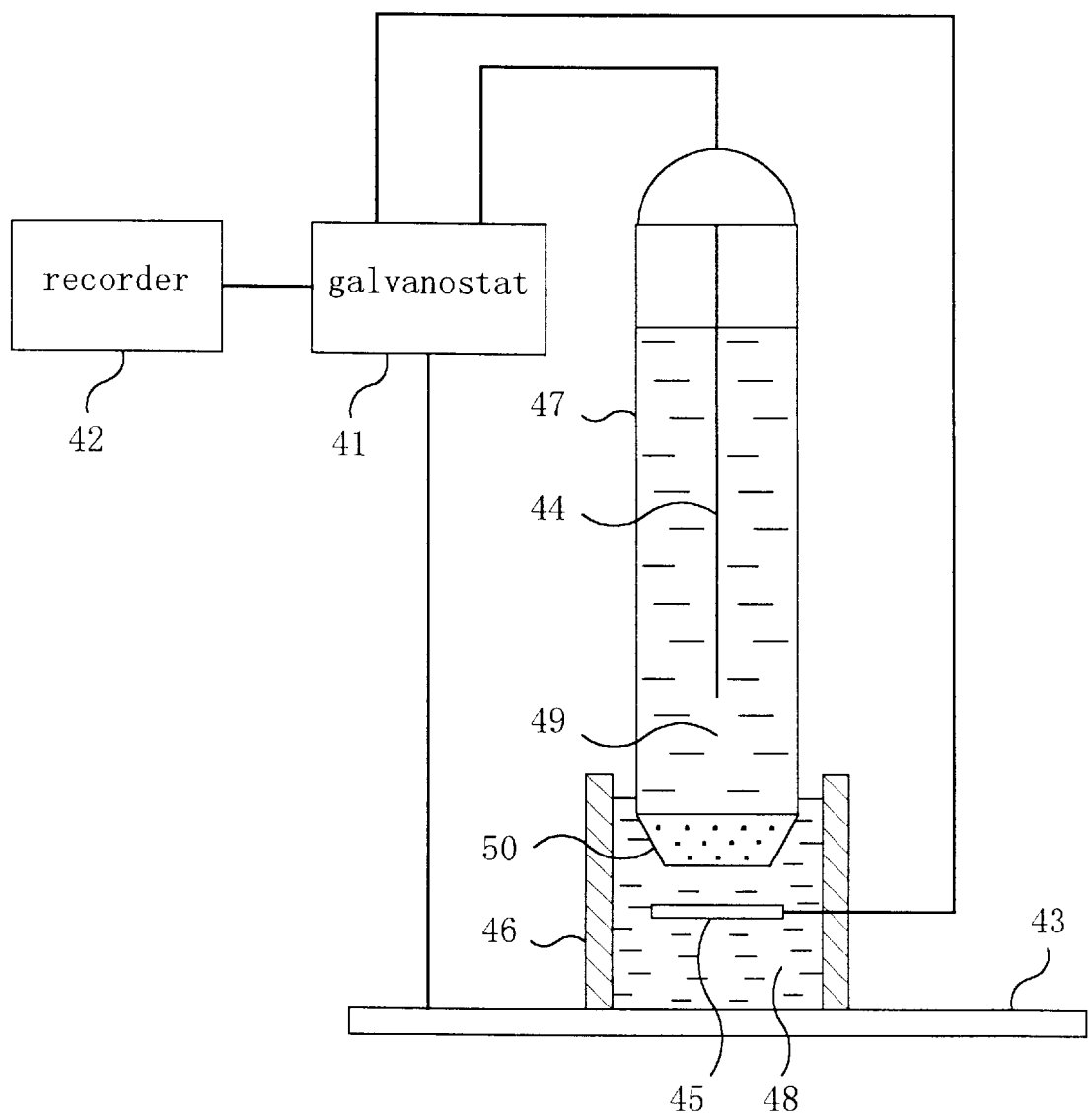
Figure 12:
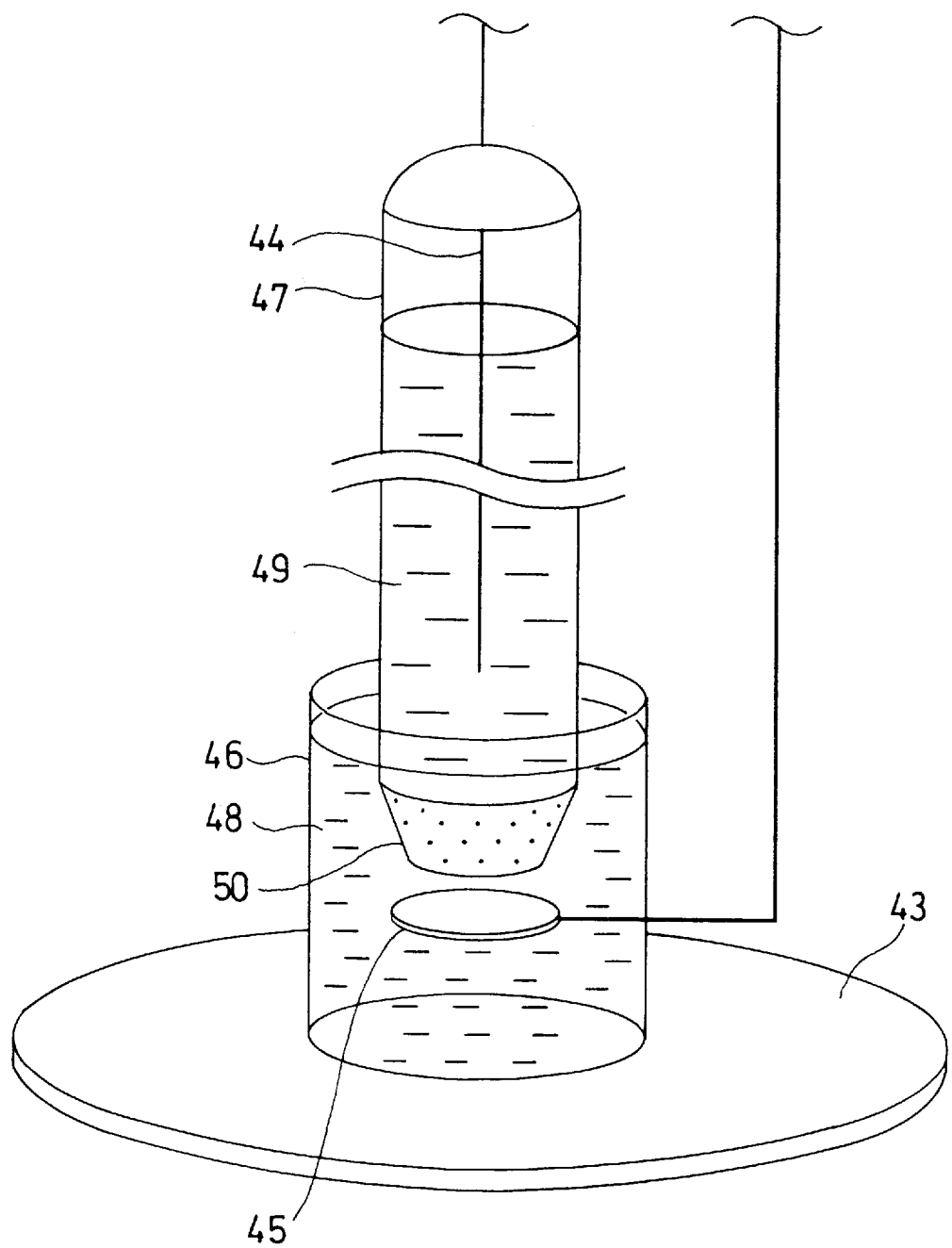
Figure 13:
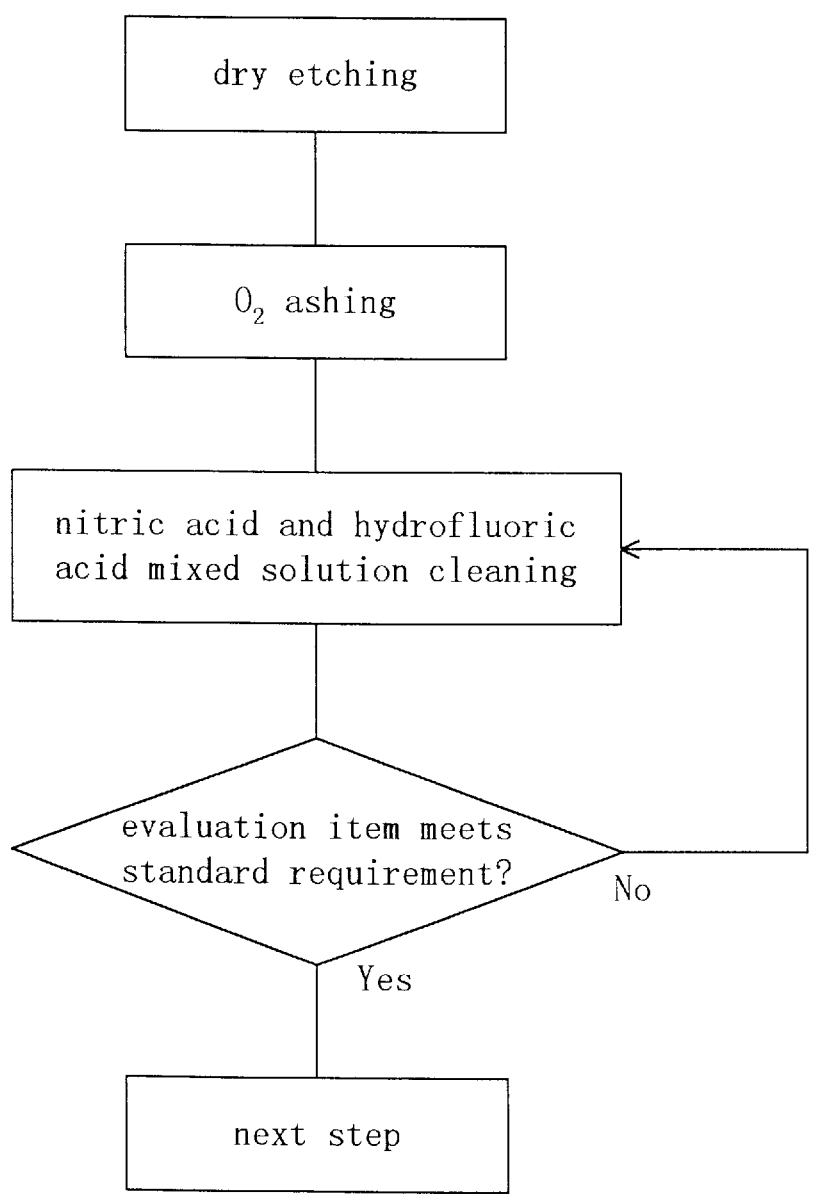
Figure 14:
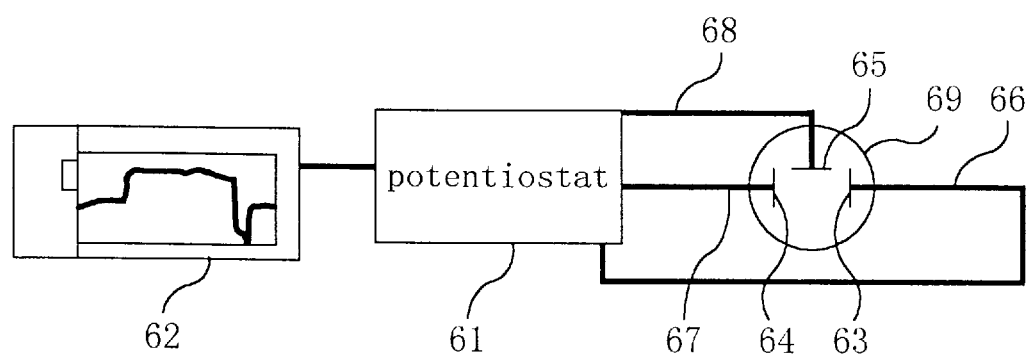
Figure 15:
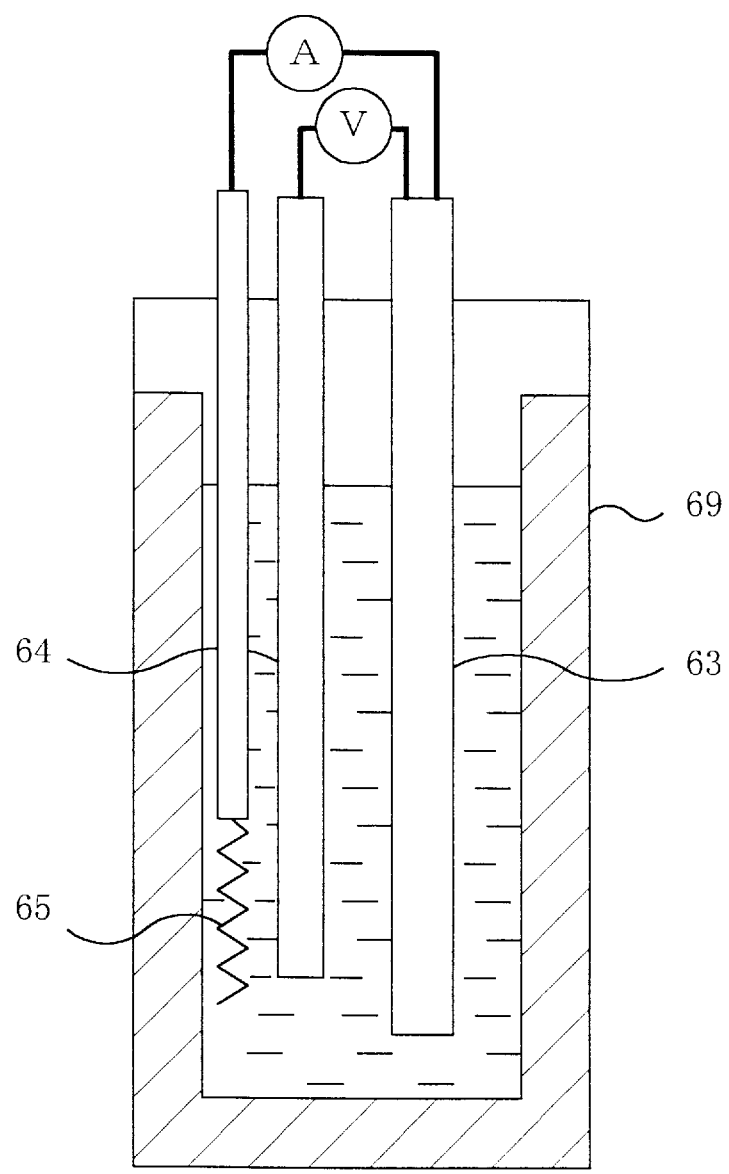
Figure 16:
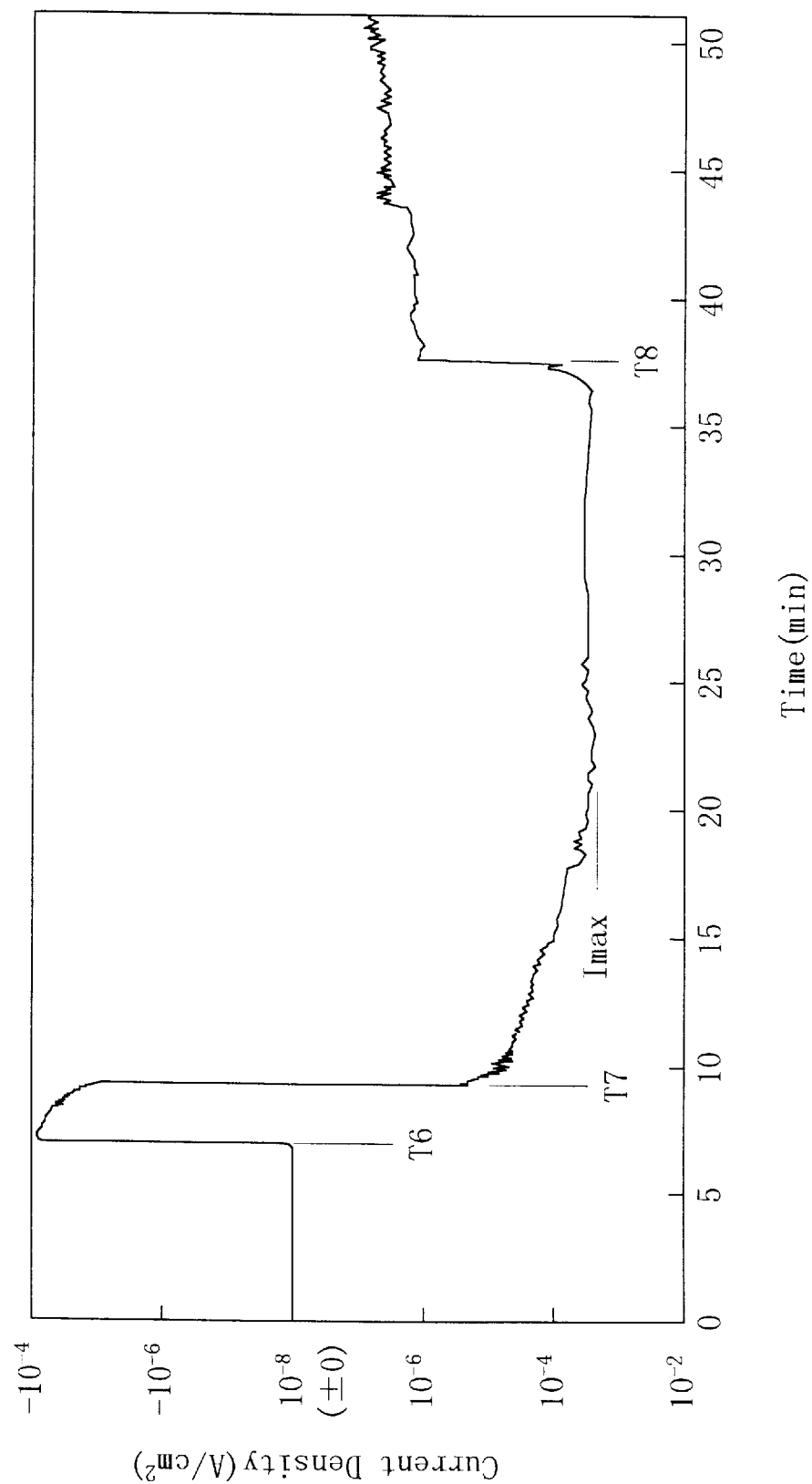
Figure 17:
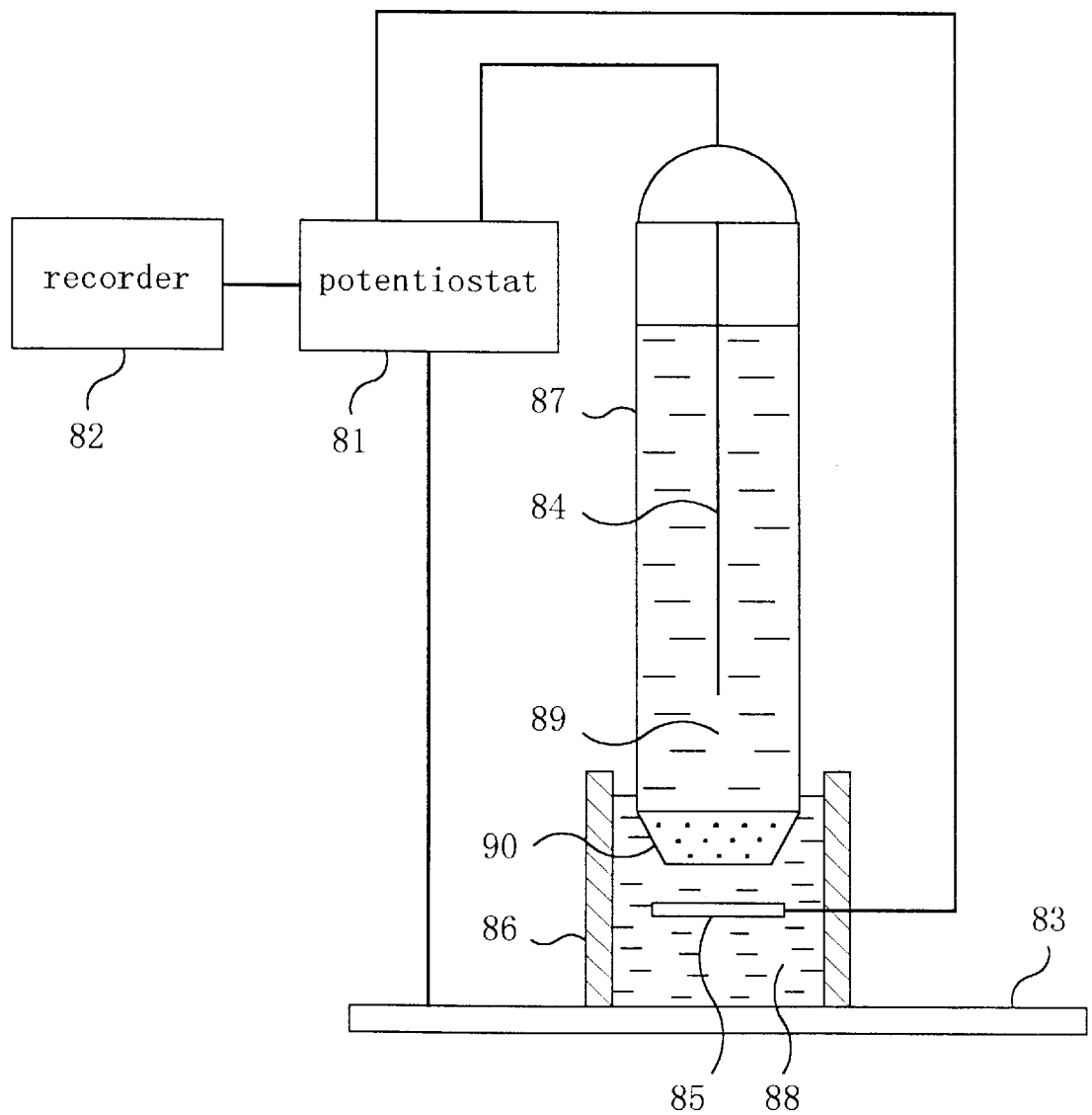
Figure 18:
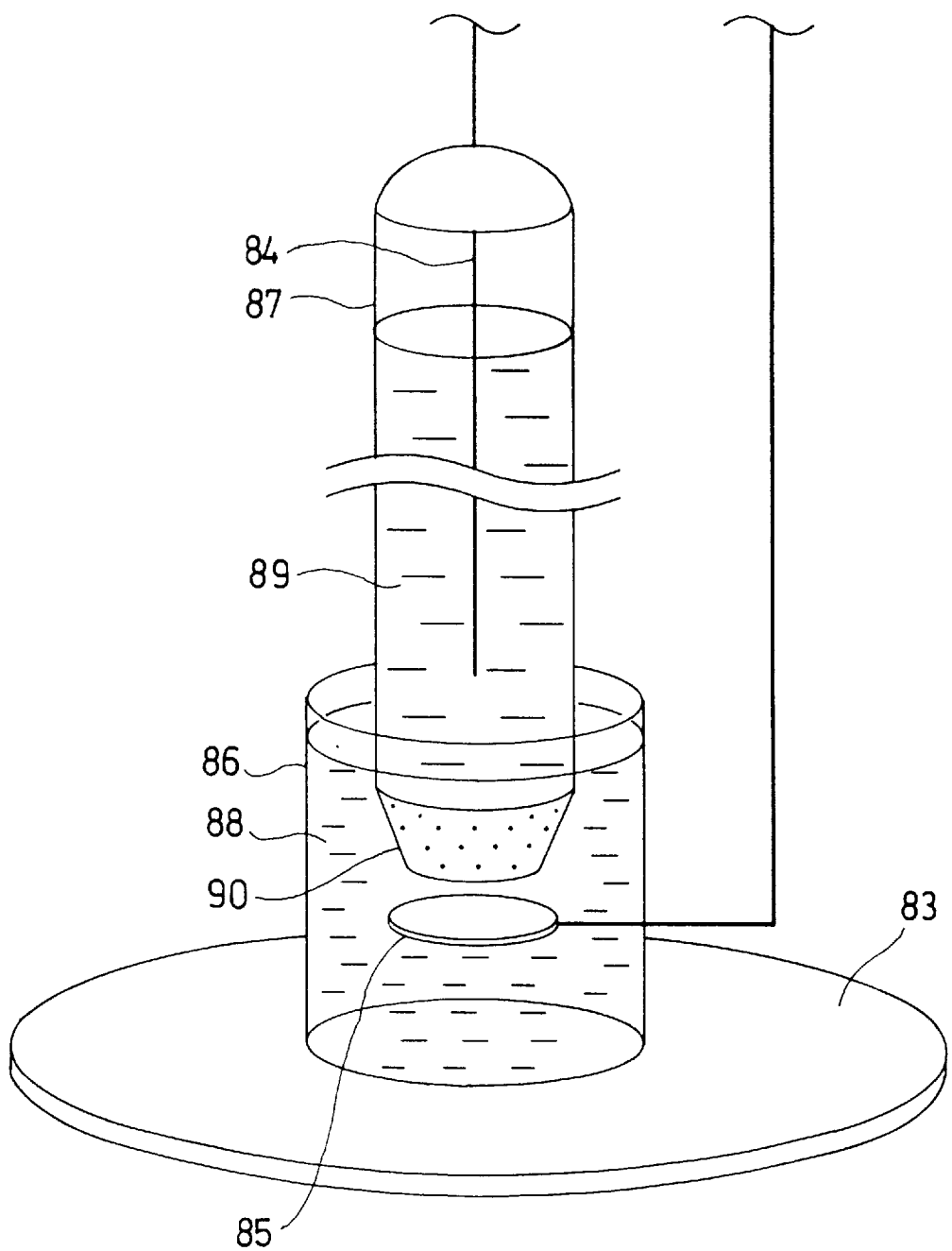

Each of FIGS. 3(a), (b), FIGS. 4(a), (b) and FIG. 5 is a view illustrating changes in electrode potential with the passage of time when constant-current electrolysis is conducted in hydrochloric acid according to the metal surface state evaluation method in accordance with the first embodiment of the present invention;

FIG. 6 is a characteristic view illustrating the relationship between time of pitting corrosion and electric current density when constant-current electrolysis is conducted in each of hydrochloric acids respectively presenting different concentrations, in the metal surface state evaluation method according to the first embodiment of the present invention;

Each of FIGS. 7(a) and (b) is a section view illustrating courses of metal corrosion in the metal surface state evaluation method according to the first embodiment of the present invention;

FIG. 8 is a characteristic view illustrating the relationship between the concentration of hydrochloric acid and graphic slope obtained through constant-current electrolysis in the metal surf ace state evaluation method according to the first embodiment of the present invention;

FIG. 9 is a view illustrating a critical electric current value in the metal surf ace state evaluation method according to the first embodiment of the present invention;

FIG. 10 is a characteristic view illustrating the relationship between time of pitting corrosion and electric current density when each of AlCu metals having different grain sizes is subjected to constant-current electrolysis in hydrochloric acid, in the metal surf ace state evaluation method according to the first embodiment of the present invention;

FIG. 11 is a general view of a measurement apparatus to be used in a metal surface state evaluation method according to a second embodiment of the present invention;

FIG. 12 is a detailed view of the measurement apparatus to be used in the metal surface state evaluation method according to the second embodiment of the present invention;

FIG. 13 is a flow chart of the steps of a semiconductor device production method according to each of third and ninth embodiments of the present invention;

FIG. 14 is a schematic view of a measurement apparatus used in a metal surf ace state evaluation method according to a seventh embodiment of the present invention;

FIG. 15 is a detailed view of the measurement apparatus used in the metal surface state evaluation method according to the seventh embodiment of the present invention;

FIG. 16 is a view illustrating changes in corrosion current with the passage of time when constant-potential electrolysis is conducted in hydrochloric acid, in the metal surface state evaluation method according to the seventh embodiment of the present invention;

FIG. 17 is a general view of a measurement apparatus used in a metal surf ace state evaluation method according to an eighth embodiment of the present invention; and FIG. 18 is a detailed view of the measurement apparatus used in the metal surface state evaluation method according to the eighth embodiment of the present invention.

DETAILED DESCRIPTION OF THE INVENTION (First Embodiment)

Figure 1:
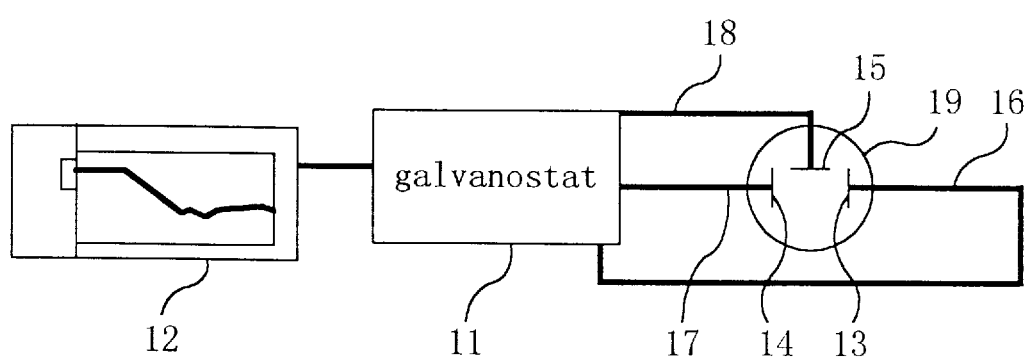
FIG. 1 is a schematic view of a measurement apparatus to be used in a metal surface state evaluation method according to a first embodiment of the present invention.
Figure 2:
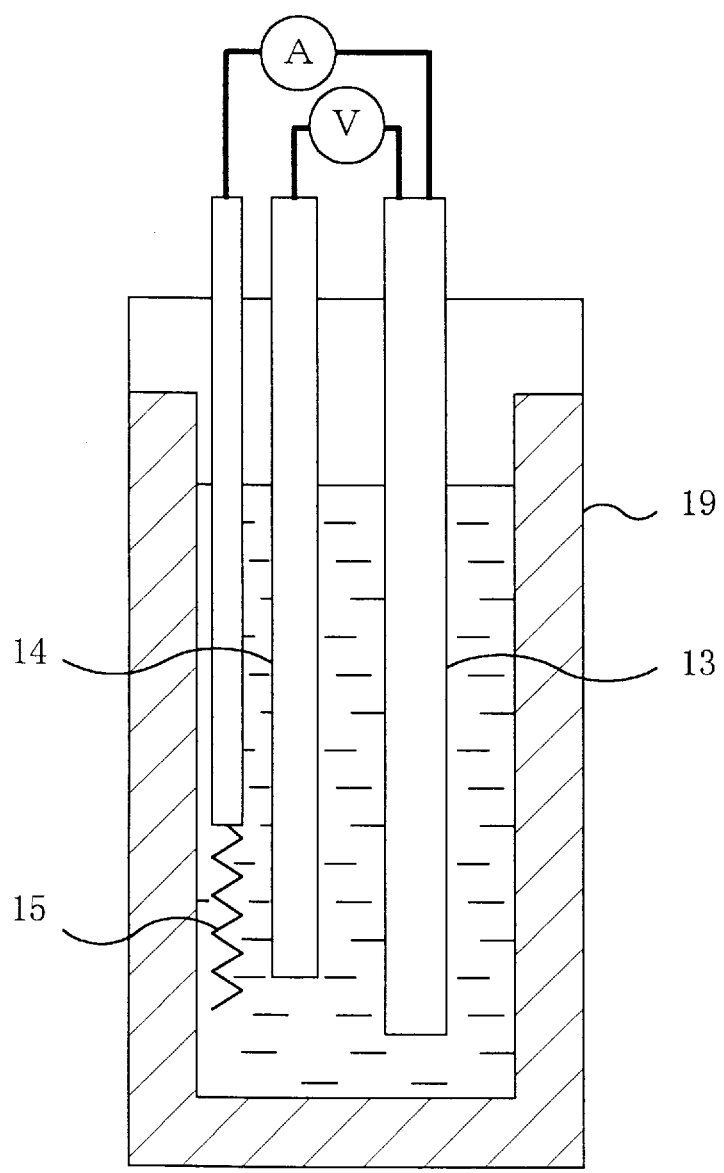
FIG. 2 is a detailed view of the measurement apparatus to be used in the metal surface state evaluation method according to the first embodiment of the present invention; of applying, to the solution, each of a plurality of constant electric currents respectively having different current values, causing the metallic wiring to be corroded by the solution; an electrode potential measuring step of measuring, at each of the electric currents, the electrode potential of the metallic wiring which is being corroded by the solution; a change ratio calculating step of calculating, based on the electrode potential at each of the electric currents, a ratio of changes in time of pitting corrosion to changes in current value; a corrosion resistance evaluating step of evaluating the corrosion resistance of the oxide layer based on the change ratio; and an oxide layer judging step of comparing the corrosion resistance of the oxide layer with a predetermined standard, whereby the oxide layer is removed and a new oxide layer is then formed when the corrosion resistance of the first mentioned oxide layer does not satisfy the predetermined standard, or the process at the subsequent step is executed on the semiconductor substrate having the oxide layer formed thereon when the corrosion resistance of the oxide layer satisfies the predetermined standard.

With reference to FIGS. 1 and 2, the following description will discuss a measurement apparatus to be used in a metal surface state evaluation method according to a first embodiment of the present invention.

FIG. 1 shows a schematic arrangement of the measurement apparatus, while FIG. 2 shows in detail the same. This measurement apparatus is arranged to measure, at a constant electric current in a solution, the electrode potential of an Al alloy layer which is a metallic thin layer for wiring (metallic wiring layer) on a semiconductor wafer serving as a semiconductor substrate.

Shown in FIGS. 1 and 2 are a galvanostat 11 for measuring a natural electrode potential, a recorder 12 for recording changes in potential with the passage of time, and a semiconductor wafer 13 on which deposited is a sample to be measured or an Al alloy layer serving as the metallic wiring layer. Also shown in FIGS. 1 and 2 are a reference electrode 14 made of Ag/AgCl, a counter electrode 15 made of Pt, and connection wiring lines 16, 17, 18 for respectively connecting the semiconductor wafer 13, the reference electrode 14 and the counter electrode 15 to the galvanostat 11. By immersing the semiconductor wafer 13, the reference electrode 14 and the counter electrode 15 in a measurement cell 19 filled with a solution, changes in electrode potential with the passage of time can be measured. Provision is made such that, when applied, an electric current flows from the galvanostat 11 to the semiconductor wafer 13 through the counter electrode 15, and that the galvanostat 11 reads a difference in potential between the reference electrode 14 and the semiconductor wafer 13.

With reference to FIGS. 3 to 10, the following description will discuss a metal surface state evaluation method of conducting an electrical chemical evaluation using the measurement apparatus having the arrangement above-mentioned.

Figure 3B:
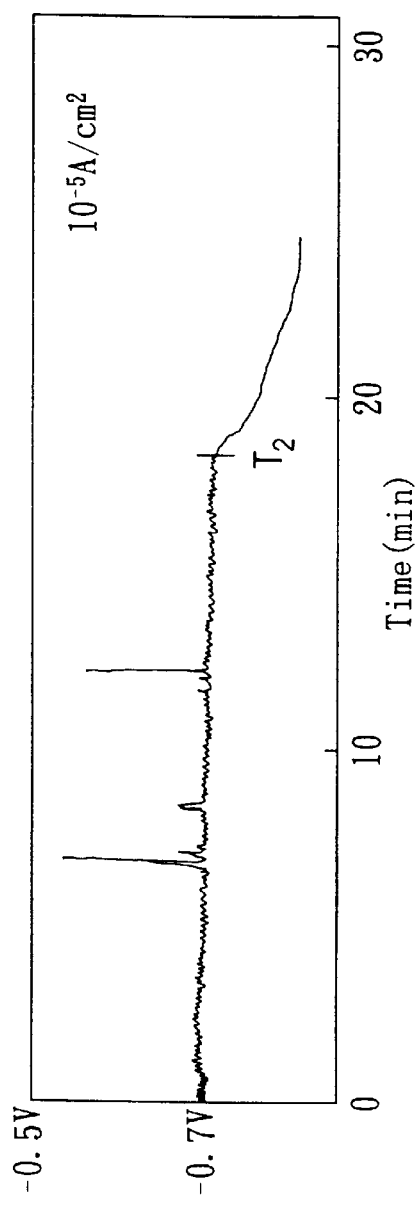
Figure 4B:
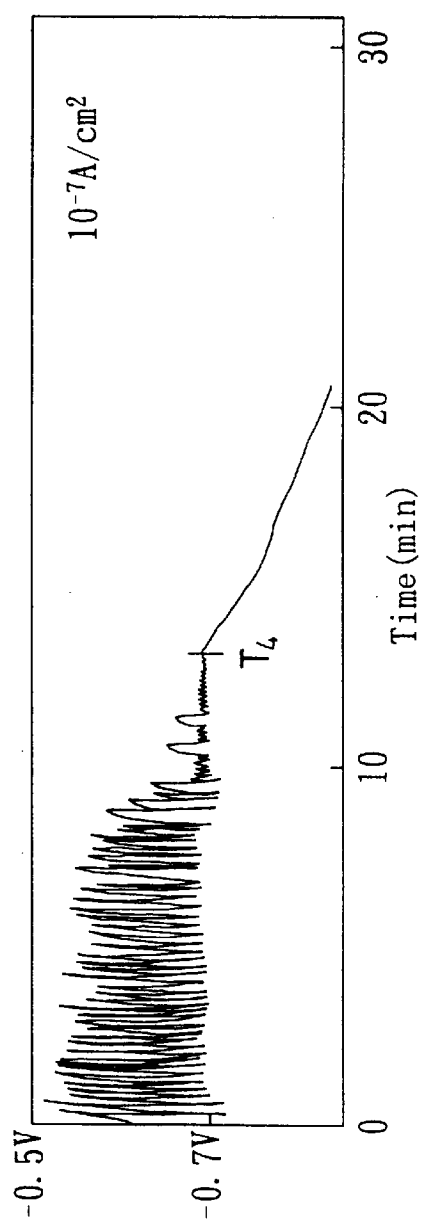

FIGS. 3 to 5 show changes in potential with the passage of time when AlSiCu thin layers were subjected to constant-current electrolysis in a 1N (normality)-hydrochloric acid solution using constant electric currents respectively having different current values (current density values).

As the solution, a hydrochloric acid solution was used because chlorine ions are liable to corrode aluminum. However, such a solution of hydrochloric acid is not necessarily required as far as the solution generates halogen ions.

From the changes with the passage of time in FIGS. 3 to 5, there can be read, at the respective constant current values (constant current density values), periods of time during which aluminum oxide layers formed on the AlSiCu thin layers were pitted and corroded by a cathodic action of Cu in the hydrochloric acid. In FIGS. 3 to 5, the time zones of 0 to $T_1-T_5$ where the values of potential fluctuate, are times of pitting corrosion during which the aluminum oxide layers are being pitted and corroded.

After the passage of times of $T_1-T_5$, a number of corroded pits are generated and the aluminum oxide layers finally disappear such that the AlSiCu thin layers are evenly corroded in their entirety. That is, the whole surfaces are corroded. In FIGS. 3 to 5, the time zones after $T_1$ to $T_5$ where the values of potential are monotonously lowered, are times of whole surface corrosion during which the whole surfaces are being corroded. It is therefore possible to clearly distinguish the times of pitting corrosion of 0 to $T_1-T_5$ during which the potential values fluctuate, from the time of whole surface corrosion during which the potentials are monotonously lowered.

The following description will discuss a mechanism of generating pitting corrosion with reference to FIG. 7(a) and (b).

Figure 7B:
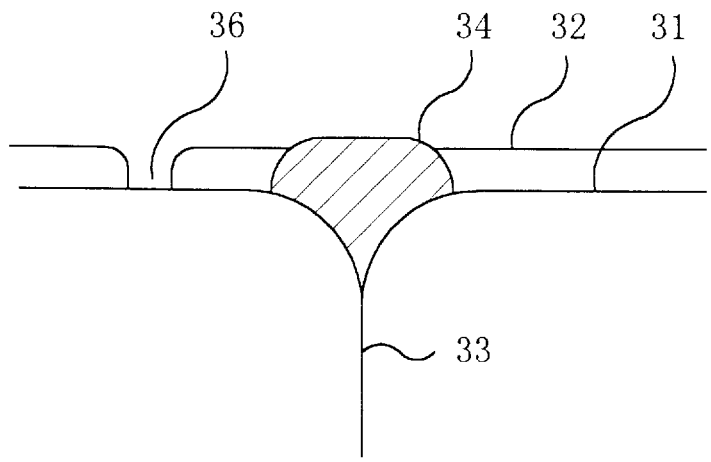

FIG. 7(a) shows a state where an aluminum oxide layer 32 as an oxide layer is formed on the surface of an AlSiCu alloy 31. Copper 34 is segregated on a boundary of aluminum crystal grains 33, and a copper oxide layer 35 is formed on the surface of the copper 34. When the sample shown in FIG. 7(a) is immersed in a hydrochloric acid solution and a constant electric current is let flow therein, the aluminum oxide layer 32 and the copper oxide layer 35 dissolve. Accordingly, as shown in FIG. 7(b), the copper 34 is exposed to the outside, causing the same to act as a cathode in the hydrochloric acid. In such a state, there is formed a difference in potential between the hydrochloric acid and the AlSiCu alloy 31 such that an electric field acts on the aluminum oxide layer 32. This results in formation of an opening 36. Such a phenomenon that the opening 36 is formed in the aluminum oxide layer 32, refers to pitting corrosion.

FIG. 6 shows the data obtained by subjecting wiring AlSiCu thin layers immediately after formed by sputtering, to constant-current electrolysis in hydrochloric acids respectively representing different concentrations with the use of constant electric currents respectively having different current values. In FIG. 6, the data are shown in the form of a graph in which the axis of ordinate represents the time of pitting corrosion measured in the manner mentioned earlier and the axis of abscissa represents, in the form of a logarithm, the current density of an applied constant electric current. In FIG. 6, graphic lines (a), (b) and (c) show relationships between time of pitting corrosion and current density (current value), as obtained through constant current electrolysis in a 0.1N-hydrochloric acid, a 1N-hydrochloric acid and a 2Nhydrochloric acid, respectively.

From FIG. 6 showing the data obtained by conducting constant-current electrolysis with the hydrochloric acid changed in concentration, it is understood that the dependency of the time of pitting corrosion on the current value varies with changes in concentration of the hydrochloric acid. More specifically, as the hydrochloric acid is higher in concentration or as the dissolving speed is faster, the dependency of the time of pitting corrosion on the current value is lowered and the slope of a graphic line in FIG. 6 is smaller. That is, when the hydrochloric acid is high in concentration, pitting corrosion due to copper is not predominating. Thus, even though the current value is increased, the time of pitting corrosion is not increased. In this connection, there is established a first relationship that, in a metallic oxide, as the slope of a graphic line indicative of the relationship between current value and time of pitting corrosion of the oxide is smaller, the oxide is more liable to be corroded in a solution irrespectively of the current value. Accordingly, by obtaining the slope of graphic line above-mentioned, the corrosion resistance of a metallic oxide or the pitting corrosion of an oxide layer on the metal surface with respect to corrosion can be evaluated.

In FIG. 8, the axis of ordinate represents the slope of each of the graphic lines (a), (b) and (c) in FIG. 6 indicative of the relationship between time of pitting corrosion and current density (current value), and the axis of abscissa represents the concentration of hydrochloric acid shown in the form of a logarithm. In FIG. 8, there is obtained a straight line of which slope with respect to the concentration of hydrochloric acid is −5.3.

On the other hand, the dissolving, by hydrochloric acid, of the aluminum oxide layer ($Al_2O_3$) serving as the oxide layer on the AlSiCu thin layer, can be expressed in the following formula (1):

$$Al_2O_3 + 6HCl \overset{k}{\rightarrow} 2AlCl_3 + 3H_2O \qquad (1)$$

wherein k is a reaction speed constant.

As shown in the following formula (2), the dissolving speed of $Al_2O_3$ is proportional to the sixth power of the concentration of hydrochloric acid:

$$-d[Al_2O_3]/dt = k[HCl]^6 \qquad (2)$$

On the other hand, the following two points are understood from the graph in FIG. 8.

Firstly, it is understood that, with an increase in concentration of hydrochloric acid, the ratio of changes in time of pitting corrosion to changes in current density or current value (the value of "graphic slope" on the axis of ordinate in FIG. 8) becomes smaller due to a negative sign of the graphic line in FIG. 8 and the aluminum oxide layer is more readily corroded.

Secondly, it is understood that, since the slope of the graphic line in FIG. 8 is −5.3, the ratio of changes in time of pitting corrosion to changes in current density is proportional to the −5.3th power of the concentration of hydrochloric acid. It is understood that, with the meaning of the negative sign taken into consideration, the corrodibility of the aluminum oxide layer is proportional to the 5.3th power of the concentration of hydrochloric acid.

The exponent of the concentration of hydrochloric acid indicative of the dissolving speed of the aluminum oxide layer ($Al_2O_3$), is equal to the value of the slope of the graphic line in FIG. 8 or the value represented by the formula (2). The slope in FIG. 8 and the value of the formula (2) are respectively equal to 5.3 and 6, which are approximate to each other. In this connection, the slope value of the graphic line in FIG. 8 refers to the dissolving speed of the aluminum oxide layer ($A_2O_3$).

More specifically, there are obtained the slopes of graphic lines, in FIG. 6, each indicative of the relationship between time of pitting corrosion and current density as obtained by a constant-current electrolysis method, and the slopes of graphic lines thus obtained are plotted with respect to the concentrations of hydrochloric acids, thus providing the graphic line in FIG. 8. A slope value of the graphic line in FIG. 8 is indicative of the dissolving speed of an oxide layer formed on the metal surface. Accordingly, by obtaining a slope value of the graphic line in FIG. 8, the dissolving speed of the oxide layer can be measured.

As a general nature, there is a second relationship that, as the metal surface is lower in smoothness, the dissolving speed is greater.

Thus, metal having a surface to be evaluated for its state, is subjected to constant-current electrolysis in a solution, and the relationship between current value and time of pitting corrosion is measured. Based on the relationship thus measured, the dissolving speed of an oxide layer on the metal surface can be measured. Accordingly, there can be evaluated the smoothness and pitting corrosion resistance of the metal surface each of which relates to the dissolving speed of the oxide layer.

In FIG. 6, the graphic line (d) shows the relationship between current density (current value) and time of pitting corrosion as obtained by subjecting an AlSiCu thin layer thermally treated for five minutes at a temperature of 450 EC, to constant-current electrolysis in 0.1N-hydrochloric acid. As shown in FIG. 6, the slope of the graphic line (d) is substantially the same as that of the graphic line (a) showing such a relationship obtained from an AlSiCu thin layer which was immersed, immediately after sputtering, in 0.1N-hydrochloric acid. It is therefore understood that, even though the metal is thermally treated, the smoothness and pitting corrosion resistance of the metal surface undergo no change.

Next, there are obtained the critical current values (=$I_{crit}$) of an AlSiCu thin layer immediately after formed by sputtering and an AlSiCu thin layer after a thermal treatment. As shown in FIG. 9, a critical current value refers to an X-intersect obtained by extending a graphic line indicative of the relationship between current value and time of pitting corrosion in the negative direction of the current value. That is, the critical current is a minimum current value at which pitting corrosion starts occurring. Accordingly, when the critical current value is small, this means that pitting corrosion readily occurs. Thus, by obtaining the critical current value, metal can be evaluated for pitting corrosion properties.

Here, using the graphic lines (a) and (d) in FIG. 6, the critical current values are obtained. The critical current value for the AlSiCu thin layer immediately after sputtering, is $1.2 \times 10^{-11}$ ($A/cm^2$) from the graphic line (a), and the critical current value for the thermally treated AlSiCu thin layer is $2.7 \times 10^{-24}$ ($A/cm^2$) from the graphic line (d). Thus, the critical current value for the thermally treated AlSiCu thin layer is reduced by 13 digits as compared with that for the AlSiCu thin layer immediately after sputtering. More specifically, when the thin layer is thermally treated, the amount of copper segregated at the grain boundary is increased, causing the layer to be readily pitted and corroded to lower the critical current value. Thus, the segregation amount or concentration of copper in the AlSiCu thin layer can be evaluated. That is, by obtaining the critical current value, the segregation amount or concentration of contained trace metal can be evaluated.

FIG. 10 shows the relationship between current density and time of pitting corrosion when AlCu thin layers of which grain sizes are different by 10 to 15 times from each other, were subjected to constant-current electrolysis. In FIG. 10, the graphic line (a) shows the relationship above-mentioned in an AlCu thin layer having a grain size of 2 to 3 $\mu$m, while the graphic line (b) shows the relationship above-mentioned in the AlCu thin layer having a grain size of 0.2 $\mu$m.

As apparent from FIG. 10, the critical current value for the AlCu thin layer having a grain size of 2 to 3 $\mu$m shown by the graphic line (a), is $1.4 \times 10^{-8}$ ($A/cm^2$) and the critical current value for the AlCu thin layer having a grain size of 0.2 $\mu$m shown by the graphic line (b), is $1.4 \times 1\ 0^{-14}$ ($A/cm^2$). Thus, the critical current value for an AlCu thin layer having a greater grain size, is greater than the critical current value of an AlCu thin layer having a smaller grain size. That is, as the grain size is greater, the grain boundary length is shorter and the amount of copper segregated on the grain boundary is reduced to restrain corrosion due to a local battery effect. Accordingly, by obtaining a critical current value, the grain boundary length or grain size of Al in the AlCu thin layer can be evaluated. More specifically, by obtaining a critical current value, the grain boundary length or grain size of Al can be evaluated.

Thus, metal having a surface to be evaluated for its state, is subjected to constant-current electrolysis in a solution, the electrode potential is measured and the relationship between current value and time of pitting corrosion is measured. Based on the relationship thus measured, the critical current value of the metal can be obtained. From the critical current value thus obtained, the metal can be evaluated for resistance to pitting corrosion, the segregation amount or concentration of contained trace metal and the grain boundary length or grain size of Al.

Accordingly, metal having a surface to be evaluated for its state, is subjected to constant-current electrolysis in a solution, the electrode potential is measured, the ratio of changes in time of pitting corrosion to changes in applied current value is obtained based on changes in electrode potential with the passage of time, the dissolving speed of the oxide layer on the metal surface is measured based on the change ratio thus obtained, and the smoothness and pitting corrosion resistance of the metal surface can be evaluated based on the dissolving speed thus measured. Further, based on the relationship between applied current value and time of pitting corrosion, the critical current value of the metal is calculated, and based on the critical current value thus calculated, the metal can be evaluated for resistance to pitting corrosion, the segregation amount or concentration of contained trace metal, the grain boundary length or grain size of the Al. Thus, the resistance to corrosion of the metal can be evaluated.

According to the first embodiment, a sample to be measured is subjected to constant-current electrolysis in hydrochloric acid, the electrode potential is measured, and changes in electrode potential with the passage of time are measured to obtain the relationship between current value and time of pitting corrosion. Based on the relationship thus obtained, the metal can be evaluated for surface smoothness, the pitting corrosion resistance of the metal surface, resistance to pitting corrosion, the segregation amount or concentration of contained trace metal, the grain boundary length or grain size of Al and the general corrosion resistance with these chemical and physical properties put together, such evaluation being made in an in-line manner in a short period of time without breaking the metal.

Accordingly, any occurrence of corrosion of metal in a metal or wiring forming process can be monitored in an in-line manner in a short period of time without breaking the semiconductor wafer. This greatly contributes to improvements in production yield of semiconductor devices. Further, when a metallic wiring layer after dry-etched is evaluated for chemical and physical properties, the results of evaluation on the dry-etching and postprocessings can be fed back into the metal or wiring forming process.
(Second Embodiment)

With reference to FIGS. 11 and 12, the following description will discuss a metal surface state evaluation method according to a second embodiment of the present invention and a measurement apparatus to be used in the method above-mentioned.

FIG. 11 shows a general arrangement of the measurement apparatus capable of measuring the potential of a very small region in the metal surface state evaluation method according to the second embodiment of the present invention. FIG. 12 shows in detail the measurement apparatus in FIG. 11.

Shown in FIGS. 11 and 12 are a galvanostat 41 for measuring an electrode potential at a constant electric current, a recorder 42 for recording changes in potential with the passage of time, and a semiconductor wafer 43 on which deposited is a sample to be measured or an Al alloy layer serving as the metallic wiring layer. Also shown in FIGS. 11 and 12 are a reference electrode 44 made of Ag/AgCl, a counter electrode 45 made of Pt, a first container 46 to be filled with a first solution 48 such as a HC1 solution or the like, and a second container 47 to be filled with a second solution 49 such as a NaCl solution, KC1 solution or the like. A crosslinking portion 50 made of a porous body such as Vycor glass or the like, prevents an exchange of the first solution 48 for the second solution 49.

The reference electrode 44, the counter electrode 45 and the first container 46 are made in a unitary structure. The first container 46 is made of a cylindrical body having a diameter of about 1 cm and a height of about 3 cm. The first container 46 is made of a material, such as glass, fluorocarbon or the like, which is not reactive to the first solution 48 and which prevents the first solution 48 from percolating to the outside.

Metal will be evaluated for surface state using the measurement apparatus having the arrangement above-mentioned in the following manner.

First, a very small region to be evaluated on the semiconductor wafer 43 is brought to close contact with the lower end of the first container 46, and the first container 46 is filled with the first solution 48.

Then, a constant current is applied to the counter electrode 45, a sample to be measured or a metallic wiring layer is subjected to constant-current electrolysis, and the electrode potential of the metallic wiring layer is measured.

Then, to measure the electrode potential of another very small region on the semiconductor wafer 43, the inside of the first container 46 is cleaned, the first solution 48 is replaced with new one, a constant electric current is applied to the counter electrode 45 in another very small region on the semiconductor wafer 43 and the electrode potential of the metallic wiring layer on another very small region is measured. Based on the electrode potential thus measured, there are calculated the ratio of changes in time of pitting corrosion to changes in current value and the critical current value, based on which the metal surface is evaluated.

According to the evaluation method above-mentioned, the metallic wiring layer on the semiconductor wafer 43 can be monitored at a plurality of points thereof in a short period of time without breaking the semiconductor wafer 43.

According to the second embodiment, the semiconductor wafer 43 can be monitored at a plurality of very small regions thereof using the evaluation method above-mentioned and the measurement apparatus above-mentioned. It is therefore possible to check variations of the metal surface state within a plane of the semiconductor wafer 43 and to obtain the average of such variations. Thus, the surface state of the metallic wiring layer on the semiconductor wafer 43 can more accurately be evaluated in a short period of time without breaking the semiconductor wafer.
(Third Embodiment)

With reference to FIG. 13, the following description will discuss a semiconductor device production method according to a third embodiment of the present invention.

FIG. 13 is a flow chart illustrating the steps to be carried out when the metal surface state evaluation method according to each of the first and second embodiments of the present invention is applied to a semiconductor device production process.

In the semiconductor device production process, 02 ashing is conducted to remove a resist after dry-etching as a wiring forming step, and a nitric acid and hydrofluoric acid mixed solution cleaning treatment is then conducted for cleaning the semiconductor wafer to restrain the metallic thin layer as a wiring layer from being corroded by residual chlorine ions. The nitric acid and hydrofluoric acid mixed solution cleaning treatment causes an oxide layer to be formed on the metallic wiring layer to prevent the same from being corroded.

According to the third embodiment, after the nitric acid and hydrofluoric acid mixed solution cleaning treatment, the metal surface state evaluation method according to each of the first and second embodiments is utilized at an evaluation step of evaluating the pitting corrosion resistance of the oxide layer formed on the metallic wiring layer after cleaned using nitric acid and hydrofluoric acid mixed solution, the corrosion resistance of the metal or the segregation amount of contained trace metal. At the evaluation step, it can be judged whether or not the evaluation items meet standard requirements, and each semiconductor wafer below standards is selected. Then, such a semiconductor wafer below standards is, for example, oxidized again by a nitric acid and hydrofluoric acid mixed solution treatment to increase the thickness of the surface layer such that the pitting corrosion resistance is increased until the semiconductor wafer meets standard requirements. This greatly contributes to improvements in production yield of semiconductor devices.
(Fourth Embodiment)

The following description will discuss a semiconductor device production method according to a fourth embodiment of the present invention.

To determine the conditions of depositing a metallic wiring layer in a semiconductor device production process, the metal surface state evaluation method according to each of the first and second embodiments is applied immediately after the metallic wiring layer has been deposited. More specifically, a metallic wiring layer immediately after deposited on the semiconductor wafer, is subjected to constant-current electrolysis, and there are measured the ratio of changes in time of pitting corrosion to changes in applied current value, and the critical current value.

Based on the ratio of changes and critical current values thus measured, the metallic wiring layer immediately after deposited can be evaluated for corrosion resistance and surface state in a short period of time. It is therefore possible to judge, in a short period of time, whether or not the metallic wiring layer deposit conditions are suitable.

(Fifth Embodiment)

The following description will discuss a method of selecting a surface activation treating solution in a plating process according to a fifth embodiment of the present invention.

When plating a metal piece, it is required to perfectly remove an oxide layer on the metal surface to activate the metal surface before the metal is immersed in a plating solution. For selecting a surface activation treating solution to be used for such an activation, the metal surface state evaluation method according to the first embodiment is used.

Pieces to be plated having the same specifications are respectively immersed in a plurality of surface activation treating solutions and subjected to constant-current electrolysis according to the first embodiment under the same condition. Based on the relationship between current value and time of pitting corrosion, the dependency of time of pitting corrosion on current value is evaluated. It can be understood that, out of the plurality of surface activation treating solutions, the solution presenting the smallest dependency of time of pitting corrosion on current value or presenting the smallest slope of a graphic line showing changes in time of pitting corrosion with respect to current value, has the greatest ability of corroding the oxide layer on each piece to be plated. Accordingly, such a treating solution is selected as the best surface activation treating solution.

(Sixth Embodiment)

The following description will discuss a method of selecting a polishing solution in a semiconductor device wiring forming process according to a sixth embodiment of the present invention.

The metal surface state evaluation method according to the first embodiment is applied for selecting a polishing solution with which a piece to be polished is polished in a chemical mechanical polishing method (CMP) used as an embedded groove flattening method in a semiconductor device wiring forming process.

Pieces to be polished having the same specifications are respectively immersed in a plurality of polishing solutions and subjected to constant-current electrolysis according to the first embodiment under the same condition. Based on the relationship between current value and time of pitting corrosion obtained by the constant-current electrolysis, the dependency of time of pitting corrosion on current value is evaluated. It can be understood that, out of the plurality of polishing solutions, the solution presenting the smallest dependency of time of pitting corrosion on current value or presenting the smallest slope of a graphic line showing changes in time of pitting corrosion with respect to current value, has the greatest ability of corroding the oxide layer on each piece to be polished. Accordingly, such a polishing solution is selected as the best polishing solution.

(Seventh Embodiment)

With reference to FIGS. 14 and 15, the following description will discuss a method of electrically chemically evaluating the surface state of metal and a measurement apparatus to be used in this method, according to a seventh embodiment of the present invention.

FIG. 14 shows a schematic arrangement of the measurement apparatus to be used in the metal surface state evaluation method according to the seventh embodiment of the present, while FIG. 15 shows in detail the same. This measurement apparatus is arranged to measure, at a constant potential in a solution, the corrosion current of an Al alloy layer which is a metallic wiring layer on a semiconductor wafer.

Shown in FIGS. 14 and 15 are a potentiostat 61 for measuring a corrosion current, a recorder 62 for recording changes in corrosion current with the passage of time, and a semiconductor wafer 63 on which deposited is a sample to be measured or an Al alloy layer serving as the metallic wiring layer. Also shown in FIGS. 14 and 15 are a reference electrode 64 made of Ag/AgCl, a counter electrode 65 made of Pt, and connection wiring lines 66, 67, 68 for respectively connecting the semiconductor wafer 63, the reference electrode 64 and the counter electrode 65 to the potentiostat 61. By immersing the semiconductor wafer 63, the reference electrode 64 and the counter electrode 65 in a measurement cell 69 filled with a solution, changes in corrosion current with the passage of time can be measured while applying a potential in the vicinity of a natural electrode potential to the sample to be measured. The potentiostat 61 reads the value of an electric current flowing between the counter electrode 65 and the semiconductor wafer 63 at the time when a potential is applied to the semiconductor wafer 63 from the potentiostat 61.

The natural electrode potential refers to a potential at which no electric current flows with the balance kept between an anode reaction in which metal dissolves, and a cathode reaction in which hydrogen ions in the solution are reduced to generate hydrogen. Even though a potential equal to the natural electrode potential is applied to the sample to be measured, no corrosion current flows. Unlike a polarization characteristic measurement method of measuring a corrosion current while sweeping a potential, the application of a potential in the vicinity of the natural electrode potential to a sample to be measured, makes it possible to observe the behavior of the sample under natural corrosion in the solution without forcibly corroding the sample.

Referring to FIG. 16, the following description will discuss a metal surface state evaluation method using the measurement apparatus having the arrangement above-mentioned.

FIG. 16 shows the results of changes in corrosion current with the passage of time, as obtained when an AlSiCu thin layer was subjected to constant-potential electrolysis in a 1N (normality)-hydrochloric acid (HCl) solution.

As the solution, a hydrochloric acid solution was used because chlorine ions are liable to corrode aluminum. However, a solution of hydrochloric acid is not necessarily required as far as the solution generates halogen ions.

From FIG. 16, there can be read a period of time before pitting corrosion starts (time of no pitting corrosion) and speed at which aluminum is corroding. In FIG. 16, a period of time during which the current density (current value) is constant after a potential has been applied, i.e., from 0 to $T_6$, is a time zone where no corrosion current is generated. In such a time zone, no pitting corrosion takes place in the aluminum oxide layer.

The current density (current value) is suddenly decreased at T6 at which pitting corrosion starts occurring. The time zone from 0 to $T_6$ is time of no pitting corrosion. In a time zone (from $T_6$ to $T_7$) where, after suddenly dropped, the current density (current value) is increased to a value in the vicinity of a maximum current density (maximum current value $I_{max}$), pitting corrosion occurs in the surface layer of the AlSiCu thin layer. In a time zone (from $T_7$ to $T_8$) where, after increased to a value in the vicinity of the maximum current density (maximum current value $I_{max}$), the current density (current value) is maintained substantially at the maximum current density (maximum current value $I_{max}$), the AlSiCu thin layer is corroding.

As the time of no pitting corrosion is longer, the pitting corrosion resistance of the metal surface is greater, and as the maximum current value is smaller, the metal corrosion speed is smaller.

Thus, based on the changes, with the passage of time, in corrosion current measured by conducting constant-potential electrolysis in hydrochloric acid, the time of no pitting corrosion and maximum current value are measured. Then, the pitting corrosion resistance of the metal surface can be evaluated based on the time of no pitting corrosion, and the corrosion resistance of the metal can be evaluated based on the maximum current value.

According to the seventh embodiment, a sample to be measured is subjected to constant-potential electrolysis in hydrochloric acid, a corrosion current is measured, changes in corrosion current with the passage of time are measured to obtain time of no pitting corrosion and maximum current value, and based on the time of no pitting corrosion and maximum current value thus obtained, the pitting corrosion resistance of the layer on the metal surface and the corrosion resistance of the metal can quantitatively be evaluated in an in-line manner in a short period of time without breaking the semiconductor wafer.

Accordingly, the occurrence of corrosion in a wiring forming process can be monitored in an in-line manner in a short period of time without breaking the semiconductor wafer, thus greatly contributing to improvements in production yield of semiconductor devices. Further, when a metallic wiring layer after dry-etched is evaluated, the results of evaluation on the dry-etching and post-processings can be fed back into the wiring forming process.

(Eighth Embodiment)

With reference to FIGS. 17 and 18, the following description will discuss a metal surface state evaluation method according to an eighth embodiment of the present invention.

FIG. 17 shows a general arrangement of a measurement apparatus capable of measuring the electric current of a very small region when evaluating metal for surface state, and FIG. 18 shows in detail the measurement apparatus.

Shown in FIGS. 17 and 18 are a potentiostat 81 for measuring a corrosion current, a recorder 82 for recording changes in corrosion current with the passage of time, and a semiconductor wafer 83 on which deposited is a sample to be measured or an Al alloy layer serving as the metallic wiring layer. Also shown in FIGS. 17 and 18 are a reference electrode 84 made of Ag/AgCl, a counter electrode 85 made of Pt, a first container 86 to be filled with a first solution 88 such as a HCl solution or the like, and a second container 87 to be filled with a second solution 89 such as a NaCl solution, KCl solution or the like. A crosslinking portion 90 made of a porous body such as Vycor glass or the like, prevents an exchange of the first solution 88 for the second solution 89.

The reference electrode 84, the counter electrode 85 and the first container 86 are made in a unitary structure. The first container 86 is a cylindrical body having a diameter of about 1 cm and a height of about 3 cm. The first container 86 is made of a material, such as glass, fluorocarbon or the like, which is not reactive to the first solution 88 and which prevents the first solution 88 from percolating to the outside.

The surface state of metal will be evaluated using the measurement apparatus having the arrangement above-mentioned in the following manner.

First, a very small region to be evaluated on the semiconductor wafer 83 is brought into close contact with the lower end of the first container 86, and the first container 86 is filled with the first solution 88.

Then, a constant potential is applied from the potentiostat 81 to the semiconductor wafer 83, a sample to be measured or a metallic wiring layer is subjected to constant-potential electrolysis, :and the corrosion current of the metallic wiring layer is measured.

Then, to measure the corrosion current of another very small region on the semiconductor wafer 83, the inside of the first container 86 is cleaned and the first solution 88 is replaced with new one, a constant potential is applied to the first and second solutions 88, 89 in another very small region on the semiconductor wafer 83 and the corrosion current of the metallic wiring layer on another very small region is measured. Based on the corrosion current thus measured, the time of no pitting corrosion and the maximum current value (maximum current density) are measured to evaluate the metal surface state.

According to the evaluation method above-mentioned, the metallic wiring layer on the semiconductor wafer 83 can be monitored at a plurality of points thereof in a short period of time without breaking the semiconductor wafer 83.

According to the eighth embodiment the semiconductor wafer 83 can be monitored at a plurality of very small regions thereof using the evaluation method above-mentioned and the measurement apparatus above-mentioned. It is therefore possible to check variations of the metal surface state within a plane of the semiconductor wafer 83 an d to obtain the average of such variations. Thus, the surface state of the metallic wiring layer on the semiconductor wafer 83 can more accurately be face evaluated in a short period of time without breaking the semiconductor wafer 83.

(Ninth Embodiment)

With reference to FIG. 13, the following description will discuss a semiconductor device production method according to a ninth embodiment of the present invention.

FIG. 13 is a flow chart illustrating the steps to be carried out when the metal surface state evaluation method according to each of the seventh and eighth embodiments is applied to a semiconductor device production process.

In the semiconductor device production process, $O_2$ ashing is conducted to remove a resist after dry-etching in a wiring forming step, and a nitric acid and hydrofluoric acid mixed solution cleaning treatment is then conducted for cleaning the semiconductor wafer to restrain the metallic thin layer as a wiring layer from being corroded by residual chlorine ions. The nitric acid and hydrofluoric acid mixed solution cleaning treatment causes an oxide layer to be formed on the metallic wiring layer to prevent the same from being corroded.

According to the ninth embodiment, after the nitric acid and hydrofluoric acid mixed solution cleaning treatment, the metal surface state evaluation method according to each of the seventh and eighth embodiments is utilized at an evaluation step of evaluating the pitting corrosion resistance of the oxide layer formed on the metallic wiring layer after cleaned using nitric acid and hydrofluoric acid mixed solution, the corrosion resistance of the metal or the segregation amount of contained trace metal. At the evaluation step, it can be judged whether or not the evaluation items meet standard requirements, and each semiconductor wafer below standards is selected. Then, such a semiconductor wafer below standards is, for example, oxidized again by a nitric acid and hydrofluoric acid mixed solution treatment to increase the thickness of the surface layer such that the layer is increased in the pitting corrosion resistance until the semiconductor wafer meets standard requirements. This greatly contributes to improvements in production yield of semiconductor devices.

(Tenth Embodiment)

The following description will discuss a semiconductor device production method according to a tenth embodiment of the present invention.

To determine the conditions of depositing a metallic wiring layer in a semiconductor device production process, the metal surface state evaluation method according to each of the seventh and eighth embodiments is applied immediately after the metallic wiring layer has been deposited. More specifically, the metallic wiring layer immediately after deposited on the semiconductor wafer, is subjected to constant-potential electrolysis and the time of no pitting corrosion and maximum current value are measured based on the corrosion current.

Based on the time of no pitting corrosion and maximum current value thus measured, the metallic wiring layer immediately after deposited can be evaluated for the pitting corrosion resistance of the surface layer and corrosion resistance of the metal in a short period of time. It is therefore possible to judge, in a short period of time, whether or not the metallic wiring layer deposit conditions are suitable.

(Eleventh Embodiment)

The following description will discuss a method of selecting a polishing solution in a semiconductor device wiring forming process according to an eleventh embodiment of the present invention.

The metal surface state evaluation method according to the seventh embodiment is applied for selecting a polishing solution with which a piece to be polished is polished in a chemical mechanical polishing method (CMP) used as an embedded groove flattening method in a semiconductor device wiring forming process.

Pieces to be polished having the same specifications are respectively immersed in a plurality of polishing solutions and subjected to constant-potential electrolysis according to the seventh embodiment under the same conditions. Based on changes in corrosion current obtained by the constant-potential electrolysis, the solution presenting the most suitable corrosion speed, is selected as the best polishing solution.

In each of the embodiments above-mentioned, as the reference electrode, an Ag/AgCl electrode is used but the reference electrode is not limited to such an Ag/AgCl electrode. Further, an AlSiCu thin layer or AlCu thin layer is used as a sample to be measured, but the sample to be measured is not limited to such a layer. As far as the sample to be measured is a metallic thin layer, measurement can be made.

In the embodiments above-mentioned, the present invention is applied to the field of semiconductor device production, but may also be applied to the field of production or mounting of a liquid crystal display device.

What is claimed is:

1. A metal surface state evaluation method comprising:
   forming a metal on a substrate;
   contacting a solution containing ions to the metal to corrode the metal;
   applying, to the solution, each of a plurality of constant electric currents respectively having different current values, causing the metal to be corroded by the solution;
   measuring, at each of the electric currents, the electrode potential of the metal which is being corroded by the solution;
   calculating, based on the electrode potential at each of the electric currents, a ratio of changes in time of pitting corrosion to changes in current value;
   measuring, based on the change ratio, a speed at which there is dissolved an oxide layer formed on the surface of the metal; and
   comparing the dissolving speed of the oxide layer with a predetermined standard, whereby either;
   the oxide layer is removed and a new oxide layer is then formed when the dissolving speed of the first-mentioned oxide layer does not satisfy the predetermined standard,
   or a subsequent step is executed on the substrate having the oxide layer formed thereon when the dissolving speed of the oxide layer satisfies the predetermined standard.

2. A metal surface state evaluation method according to claim 1, further comprising evaluating the surface smoothness of the metal based on the dissolving speed.

3. A metal surface state evaluation method according to claim 1, further comprising evaluating the pitting corrosion resistance of the oxide layer based on the dissolving speed measured.

4. A metal surface state evaluation method comprising:
   forming a metal on a substrate;
   contacting a solution containing ions to the metal to corrode the metal;
   applying, to the solution, each of a plurality of constant electric currents respectively having different current values, causing the metal to be corroded by the solution;
   measuring, at each of the electric currents, the electrode potential of the metal which is being corroded by the solution;
   calculating, based on the electrode potential at each of the current values, a relationship between current value and time of pitting corrosion;
   calculating, based on the relationship between current value and time of pitting corrosion, a critical current value which is the minimum current value at which pitting corrosion starts occurring;
   evaluating the pitting corrosion property of the metal based on said critical current value; and
   comparing the pitting-corrosion property of the metal with a predetermined standard, whereby either
   the metal is removed and a new metal is then formed when the pitting-corrosion property of the first-mentioned metal does not satisfy the predetermined standard,
   or a subsequent step is executed on the substrate having the metal formed thereon when the pitting-corrosion property of the metal satisfies the predetermined standard.

5. A metal surface state evaluation method according to claim 4, further comprising evaluating the grain size or grain boundary length of the metal based on the critical current value calculated.

6. A metal surface state evaluation method comprising:
   forming an alloy containing a trace metal on a substrate;
   contacting a solution containing ions to the alloy containing a trace metal to corrode the alloy;
   applying, to the solution, each of a plurality of constant electric currents respectively having different current values, causing the alloy to be corroded by the solution;
   measuring, at each of the electric currents, the electrode potential of the alloy which is being corroded by the solution;

calculating, based on the electrode potential at each of the current values, a relationship between current value and time of pitting corrosion;

calculating, based on the relationship between current value and time of pitting corrosion, a critical current value which is the minimum current value at which pitting corrosion starts occurring;

evaluating, based on the critical current value, the segregation amount or concentration of the metal in the alloy; and comparing the segregation amount or concentration of the metal in the alloy with a predetermined standard, whereby either the alloy is removed and a new alloy is then formed when the segregation amount or concentration of the metal in the first-mentioned alloy does not satisfy the predetermined standard, or a subsequent step is executed on the substrate having the alloy formed thereon when the segregation amount or concentration of the metal in the alloy satisfies the predetermined standard.

7. A metal surface state evaluation method comprising:

forming a metallic layer on a substrate;

contacting a solution containing ions to the metallic layer to corrode the metallic layer;

applying, to the solution, each of a plurality of constant electric currents respectively having different current values, causing the metallic layer to be corroded by the solution;

measuring, at each of the electric currents, the electrode potential of the metallic layer which is being corroded by the solution;

calculating, based on, the electrode potential at each of the current values, a relationship between current value and time of pitting corrosion;

calculating, based on the electrode potential at each of the electric currents, a ratio of changes in time of pitting corrosion to changes in current value;

calculating, based on the relationship between current value and time of pitting corrosion, a critical current value which is the minimum current value at which pitting corrosion starts occurring;

evaluating the corrosion resistance of the metallic layer based on the change ratio and the critical current value; and comparing the corrosion resistance of the metallic layer with a predetermined standard, whereby either;

the metallic layer is removed and a new metallic layer is then formed when the corrosion resistance of the first-mentioned metallic layer does not satisfy the predetermined standard, or a subsequent step is executed on the substrate having the metallic layer formed thereon when the corrosion resistance of the metallic layer satisfies the predetermined standard.

8. A metal surface state evaluation method comprising:

forming a metal on a substrate;

contacting a solution containing ions to the metal to corrode the metal;

applying a constant potential to the solution, causing the metal to be corroded by the solution;

measuring changes, with the passage of time, in corrosion current of the metal which is being corroded by the solution;

measuring, based on the changes in corrosion current with the passage of time, a period of time during which no pitting corrosion is occurring;

evaluating, based on the no-pitting-corrosion time, the pitting corrosion resistance of an oxide layer formed on the surface of the metal; and comparing the pitting corrosion resistance of the oxide layer with a predetermined standard, whereby either;

the oxide layer is removed and a new oxide layer is then formed when the pitting corrosion resistance of the first-mentioned oxide layer does not satisfy the predetermined standard, or a subsequent step is executed on the substrate having the oxide layer formed thereon when the pitting corrosion resistance of the oxide layer satisfies the predetermined standard.

9. A metal surface state evaluation method according to claim 8, wherein the constant potential to be applied, has a value which is about the natural electrode potential of the metal.

10. A metal surface state evaluation method comprising:

forming a metal on a substrate;

contacting a solution containing ions to the metal to corrode the metal;

applying a constant potential to the solution, causing the metal to be corroded by the solution;

measuring the maximum corrosion current having the highest value out of corrosion currents of the metal which is being corroded by the solution;

evaluating the corrosion resistance of the metal based on the maximum corrosion current; and comparing the corrosion resistance of the metal with a predetermined standard, whereby either;

the metal is removed and a new metal is then formed when the corrosion resistance of the first-mentioned metal does not satisfy the predetermined standard, or a subsequent step is executed on the substrate having the metal formed thereon when the corrosion resistance of the metal satisfies the predetermined standard.

11. A metal surface state, evaluation method according to claim 10, wherein the constant potential to be applied, has a value which is about the natural electrode potential of the metal.

12. A semiconductor device production method comprising:

forming a metallic layer on a semiconductor substrate under predetermined deposit conditions;

contacting a solution containing ions to the metallic layer to corrode the metallic layer;

applying, to the solution, each of a plurality of constant electric currents respectively having different current values, causing the metallic layer to be corroded by the solution;

measuring, at each of the electric currents, the electrode potential of the metallic layer which is being corroded by the solution;

calculating, based on the electrode potential at each of the current values, a relationship between current value and time of pitting corrosion;

calculating, based on the electrode potential at each of the electric currents, a ratio of changes in time of pitting corrosion to changes in current value;

calculating, based on the relationship between current value and time of pitting corrosion, a critical current value which is the minimum current value at which pitting corrosion starts occurring;

evaluating the surface state of the metallic layer based on the change ratio and the critical current value;

judging, based on the evaluation thus made, whether or not the predetermined deposit conditions at the metallic layer forming step are suitable; wherein the metallic layer is removed and a new metallic layer is then formed when the surface state of the first-mentioned metallic layer does not satisfy the predetermined deposit conditions, or a subsequent step is executed on the semiconductor substrate having the metallic layer formed thereon when the surface state of the metallic layer satisfies the predetermined deposit conditions.

13. A semiconductor device production method comprising:

forming metallic wiring on a semiconductor substrate;

forming an oxide layer on the metallic wiring;

contacting a solution containing ions to the metallic wiring having the oxide layer formed thereon to corrode the metallic wiring;

applying, to the solution, each of a plurality of constant electric currents respectively having different current values, causing the metallic wiring to be corroded by the solution;

measuring, at each of the electric currents, the electrode potential of the metallic wiring which is being corroded by the solution;

calculating, based on the electrode potential at each of the electric currents, a ratio of changes in time of pitting corrosion to changes in current value;

evaluating the corrosion resistance of the oxide layer based on the change ratio; and comparing the corrosion resistance of the oxide layer with a predetermined standard, whereby either;

the oxide layer is removed and a new oxide layer is then formed when the corrosion resistance of the first-mentioned oxide layer does not satisfy the predetermined standard, or a subsequent step is executed on the semiconductor substrate having the oxide layer formed thereon when the corrosion resistance of the oxide layer satisfies the predetermined standard.

* * * * *

UNITED STATES PATENT AND TRADEMARK OFFICE
CERTIFICATE OF CORRECTION

PATENT NO. : 5,820,746
DATED : October 13, 1998
INVENTOR(S) : Akemi KAWAGUCHI et al.

It is certified that error appears in the above-identified patent and that said Letters Patent is hereby corrected as shown below:

Cover Page,

[30] Foreign Application Priority Data
Line 15, delete "Aug. 12, 1996" and
insert --March 12, 1996--.

Signed and Sealed this

Eighth Day of June, 1999

Attest:

Q. TODD DICKINSON

*Attesting Officer*   *Acting Commissioner of Patents and Trademarks*